US012590152B2

(12) United States Patent
Canestraro et al.

(10) Patent No.: US 12,590,152 B2
(45) Date of Patent: *Mar. 31, 2026

(54) CD3-SPECIFIC BINDING MOLECULES

(71) Applicant: IMMUNOCORE LIMITED, Abingdon (GB)

(72) Inventors: Martina Canestraro, Abingdon (GB); Nele Dieckmann, Abingdon (GB); Stephen Harper, Abingdon (GB); Peter Benedict Kirk, Abingdon (GB); Rachel Mulvaney, Abingdon (GB); Ronan O'Dwyer, Abingdon (GB); Ian Butler Robertson, Abingdon (GB)

(73) Assignee: IMMUNOCORE LIMITED, Abingdon (GB)

( * ) Notice: Subject to any disclaimer, the term of this patent is extended or adjusted under 35 U.S.C. 154(b) by 1137 days.

This patent is subject to a terminal disclaimer.

(21) Appl. No.: 17/427,592

(22) PCT Filed: Jan. 30, 2020

(86) PCT No.: PCT/EP2020/052315
§ 371 (c)(1),
(2) Date: Jul. 30, 2021

(87) PCT Pub. No.: WO2020/157210
PCT Pub. Date: Aug. 6, 2020

(65) Prior Publication Data
US 2022/0119527 A1 Apr. 21, 2022

(30) Foreign Application Priority Data
Jan. 30, 2019 (GB) .................................... 1901305

(51) Int. Cl.
| | |
|---|---|
| *C07K 16/28* | (2006.01) |
| *A61K 40/33* | (2025.01) |
| *C07K 16/46* | (2006.01) |
| *C12N 15/00* | (2006.01) |

(52) U.S. Cl.
CPC .......... *C07K 16/2809* (2013.01); *A61K 40/33* (2025.01); *C07K 16/46* (2013.01); *C07K 2317/24* (2013.01); *C07K 2317/31* (2013.01); *C07K 2317/565* (2013.01); *C07K 2317/567* (2013.01); *C07K 2317/622* (2013.01); *C07K 2317/73* (2013.01); *C07K 2317/92* (2013.01); *C12N 15/00* (2013.01)

(58) Field of Classification Search
CPC ............ C07K 16/2809; C07K 2317/24; C07K 2317/31; C07K 2317/565; C07K 2317/567; C07K 2317/622; C07K 2317/73; C07K 2317/92; C07K 2319/00; C07K 14/7051; C07K 16/30; C07K 2317/70; A61K 2039/505
See application file for complete search history.

(56) References Cited

U.S. PATENT DOCUMENTS

| | | | | |
|---|---|---|---|---|
| 3,773,919 | A | 11/1973 | Boswell et al. | |
| 4,485,045 | A | 11/1984 | Regen | |
| 4,544,545 | A | 10/1985 | Ryan et al. | |
| 4,619,794 | A | 10/1986 | Hauser | |
| 5,225,539 | A | 7/1993 | Winter | |
| 5,821,337 | A | 10/1998 | Carter et al. | |
| 12,065,475 | B2 * | 8/2024 | Conroy | C07K 14/7051 |
| 12,103,971 | B2 * | 10/2024 | Dembek | C07K 16/2833 |
| 12,134,647 | B2 * | 11/2024 | Jaworski | C07K 16/2809 |
| 12,195,534 | B2 * | 1/2025 | Mai | C07K 14/7051 |
| 2007/0071675 | A1 | 3/2007 | Wu et al. | |
| 2015/0166661 | A1 | 6/2015 | Chen et al. | |
| 2023/0348595 | A1 * | 11/2023 | Chillakuri | C07K 16/2833 |
| 2024/0092859 | A1 * | 3/2024 | Conroy | A61K 45/06 |
| 2024/0190969 | A1 * | 6/2024 | Chillakuri | A61K 35/17 |
| 2024/0254228 | A1 * | 8/2024 | Mai | A61P 35/00 |
| 2025/0179178 | A1 * | 6/2025 | Mai | A61P 35/00 |

FOREIGN PATENT DOCUMENTS

| | | | |
|---|---|---|---|
| DE | 3218121 | A1 | 11/1983 |
| EP | 0052522 | A2 | 5/1982 |
| EP | 0088046 | A2 | 9/1983 |
| EP | 0036676 | B1 | 7/1984 |
| EP | 0184187 | A2 | 6/1986 |
| EP | 0058481 | B1 | 10/1986 |
| EP | 0142541 | B1 | 7/1987 |
| EP | 0143949 | B1 | 10/1988 |
| EP | 0125023 | B1 | 6/1991 |
| EP | 0120694 | B1 | 7/1993 |
| EP | 0239400 | B1 | 8/1994 |
| GB | 2188638 | A | 10/1987 |
| RU | 2650868 | C2 | 4/2018 |
| WO | WO 1993/011161 | A1 | 6/1993 |
| WO | WO 1994/013804 | A1 | 6/1994 |
| WO | WO 1998/039482 | A1 | 9/1998 |

(Continued)

OTHER PUBLICATIONS

U.S. Appl. No. 18/901,016, Jaworski, Jakub.*
U.S. Appl. No. 18/966,386, Mai, Nicole.*
U.S. Appl. No. 18/004,644, Leonard, Sarah.*
U.S. Appl. No. 18/004,644, filed Jan. 6, 2023, Leonard, Sarah.*
U.S. Appl. No. 19/104,630, filed Feb. 18, 2025, Conroy, Paul.*
Falconer, R.J., et al.(2011), Stabilization of a monoclonal antibody during purification and formulation by addition of basic amino acid excipients. J. Chem. Technol. Biotechnol., 86: 942-948. https://doi.org/10.1002/jctb.2657 (Year: 2011).*
Lodish, et al. Molecular Cell Biology. 7th ed. 2012. W.H. Freeman and Co. Chapter 5. (Year: 2012).*

(Continued)

*Primary Examiner* — Maher M Haddad
*Assistant Examiner* — Alec Jon Peters
(74) *Attorney, Agent, or Firm* — Fenwick and West LLP

(57) ABSTRACT

The present invention relates to specific binding molecules which bind to CD3, particularly antibodies and fragments thereof, with improved properties.

19 Claims, 5 Drawing Sheets
Specification includes a Sequence Listing.

(56) References Cited

FOREIGN PATENT DOCUMENTS

| WO | WO 1999/018129 | A1 | 4/1999 | |
| WO | WO 2001/062908 | A2 | 8/2001 | |
| WO | WO 2001/077342 | A1 | 10/2001 | |
| WO | WO 2003/020763 | A2 | 3/2003 | |
| WO | WO 2004/033685 | A1 | 4/2004 | |
| WO | WO 2006/000830 | A2 | 1/2006 | |
| WO | WO-2010133828 | A1 * | 11/2010 | ....... A61K 39/00114 |
| WO | WO 2011/001152 | A1 | 1/2011 | |
| WO | WO 2014/012085 | A2 | 1/2014 | |
| WO | WO 2017/109496 | A1 | 6/2017 | |
| WO | WO 2017/175006 | A1 | 10/2017 | |
| WO | WO-2018234319 | A1 * | 12/2018 | ............ A61K 35/17 |

OTHER PUBLICATIONS

Arnett KL, et al. Crystal structure of a human CD3-epsilon/delta dimer in complex with a UCHT1 single-chain antibody fragment. Proc Natl Acad Sci U S A. Nov. 16, 2004;101(46):16268-73. doi: 10.1073/pnas.0407359101. Epub Nov. 8, 2004. PMID: 15534202; PMCID: PMC528977. (Year: 2004).*

Badri, H., et al., "Optimization of radiation dosing schedules for proneural glioblastoma," *Journal of Mathematical Biology*, 2016, vol. 72, pp. 1301-1336.

Baylot, V., et al., "TCTP Has a Crucial Role in the Different Stages of Prostate Cancer Malignant Progression," Results and Problems in Cell Differentiation, 2017, vol. 64, pp. 255-261.

Colman, P.M., "Effects of amino acid sequence changes on antibody-antigen interactions," Research in Immunology, vol. 145, Issue 1, 1994, pp. 33-36.

International Preliminary Report on Patentability, Chapter 1, Patent Cooperation Treaty Application No. PCT/EP2020/052316, Jul. 27, 2021, 9 pages.

International Search Report and Written Opinion, Patent Cooperation Treaty Application No. PCT/EP2020/052315, May 8, 2020, 14 pages.

Pan, Q., et al., "Blocking Neuropilin-1 Function Has an Additive Effect with Anti-VEGF to Inhibit Tumor Growth," *Cancer Cell*, 11, Jan. 2007, pp. 53-67.

Rudikoff, S. et al., "Single amino acid substitution altering antigen-binding specificity," Proceedings of the National Academy of Sciences, Mar. 1982, vol. 79, No. 6, pp. 1979-1983.

Spiess, C., et al., "Alternative molecular formats and therapeutic applications for bispecific antibodies," *Molecular Immunology*, vol. 67, Issue 2, Part A, Oct. 2015, pp. 95-106.

Altschul et al., "Basic local alignment search tool," *Journal of Molecular Biology*, vol. 215, Issue 3, Oct. 5, 1990, pp. 403-410.

Altschul et al., "Gapped BLAST and PSI-BLAST: a new generation of protein database search programs," *Nucleic Acids Research*, vol. 25, Issue 17, Sep. 1, 1997, pp. 3389-3402.

Ausubel, F.M., Brent, R., Kingston, R.E., Moore, D.D., Seidman, J.G., Smith, J.A., & Struhl, K. (Eds.), (1992), *Short Protocols in Molecular Biology*, 2nd Edition, 1992, John Wiley & Sons, 95 pages.

Baeuerle et al., "Bispecific T-Cell Engaging Antibodies for Cancer Therapy," *Cancer Research*, Jun. 15, 2009;69(12):4941-4.

Barbas et al., "In vitro evolution of a neutralizing human antibody to human immunodeficiency virus type 1 to enhance affinity and broaden strain cross-reactivity," *Proceedings of the National Academy of Science USA*, vol. 91, Issue 9, Apr. 1994, pp. 3809-3813.

Bodanzsky, M. and Bodanzsky, A. (Eds), *The Practice of Peptide Synthesis*, Springer Verlag, New York (1984).

Bragado et al., "Allelic polymorphism in the coding region of human TCR Cα gene and characterization of structural variability in the α chain constant domain," *International Immunology*, vol. 6, Issue 2, Feb. 1994, pp. 223-230.

Brinkmann et al., "The making of bispecific antibodies," Mabs, Feb.-Mar. 2017; 9(2): 182-212.

Chang et al., "Opportunities and challenges for TCR mimic antibodies in cancer therapy," *Expert Opinion on Biological Therapy*, Aug. 2016;16(8):979-87.

Dahan, R. et al., "T-cell-receptor-like antibodies—generation, function and application," Expert Reviews in Molecular Medicine, Feb. 24, 2012, vol. 14:e6, pp. 1-17.

Dennis et al., "Albumin Binding as a General Strategy for Improving the Pharmacokinetics of Proteins," *The Journal of Biological Chemistry*, Sep. 20, 2002; vol. 277, No. 38, pp. 35035-35043.

Devereux, et al., "A comprehensive set of sequence analysis programs for the VAX," Nucleic Acids Research, vol. 12, Issue 1, Part 1, Jan. 11, 1984, pp. 387-395.

Dozier et al., "Site-Specific PEGylation of Therapeutic Proteins," *International Journal of Molecular Sciences*, Oct. 28, 2015;16(10):25831-64.

Epel et al., "A functional recombinant single-chain T cell receptor fragment capable of selectively targeting antigen-presenting cells," Cancer Immunology, Immunotherapy, Nov. 2002, 51(10):565-73.

Eppstein et al., "Biological activity of liposome-encapsulated murine interferon gamma is mediated by a cell membrane receptor," *Proceedings of the National Academy of Sciences USA*, vol. 82, Issue 11, Jun. 1985, pp. 3688-3692.

Gram et al., "In vitro selection and affinity maturation of antibodies from a naive combinatorial immunoglobulin library," *Proceedings of the National Academy of Sciences USA*, vol. 89, Issue 8, Apr. 1992, pp. 3576-3580.

Hollinger, P. et al., "'Diabodies': small bivalent and bispecific antibody fragments," *Proceedings of the National Academy of Sciences USA*, vol. 90, Issue 14, Jul. 1993, pp. 6444-6448.

Hoo et al., "Characterization of a single-chain T-cell receptor expressed in *Escherichia coli,*" *Proceedings of the National Academy of Sciences*, May 1992, vol. 89; Issue 10, pp. 4759-4763.

Husain et al., "Expanding the Boundaries of Biotherapeutics with Bispecific Antibodies," *BioDrugs*, 2018, 32(5):441-464.

Huston et al., "Protein engineering of antibody binding sites: recovery of specific activity in an anti-digoxin single-chain Fv analogue produced in *Escherichia coli,*" *Proceedings of the National Academy of Sciences USA*, Aug. 1988, vol. 85, Issue 16, pp. 5879-5883.

Hwang et al., "Hepatic uptake and degradation of unilamellar sphingomyelin/cholesterol liposomes: a kinetic study," *Proceedings of the National Academy of Sciences USA*, Jul. 1980, vol. 77, Issue 7, pp. 4030-4034.

Jefferis, R., "Glycosylation as a strategy to improve antibody-based therapeutics," *Nature Reviews Drug Discovery*, Mar. 2009, vol. 8, pp. 226-234.

Jevsevar et al., "PEGylation of therapeutic proteins," *Biotechnology Journal*, Special Issue: Biotech Methods and Advances, Jan. 2010, vol. 5, Issue 1, pp. 113-128.

Karlin and Altschul, "Applications and statistics for multiple high-scoring segments in molecular sequences," *Proceedings of the National Academy of Sciences of the USA*, Jun. 1993, vol. 90, pp. 5873-5877.

Karlin and Altschul, "Methods for assessing the statistical significance of molecular sequence features by using general scoring schemes," *Proceedings of the National Academy of Sciences of the USA*, Mar. 1990, vol. 87, pp. 2264-2268.

Lefranc et al., "IMGT™, the International ImMunoGene Tics Information System," *Nucleic Acids Research*, vol. 37, Jan. 2009, pp. D1006-D1012.

Liddy, N. et al., " Monoclonal TCR-redirected tumor cell killing", *Nature Medicine*, Jun. 2012, vol. 18, No. 6, pp. 980-987.

Myers, E. W. et al., "Optimal alignments in linear space," Computer applications in the biosciences (CABIOS), Mar. 1988, vol. 4, No. 1, pp. 11-17.

Pearson and Lipman, "Improved tools for biological sequence comparison," PNAS, Apr. 1988, 85 (8) 2444-2448; https://doi.org/10.1073/pnas.85.8.2444.

Plückthun, "Antibody Engineering: Advances from the Use of *Escherichia coli* Expression Systems," Nature Biotechnology, Jun. 1991, vol. 9, No. 6, pp. 545-551.

(56)                    References Cited

OTHER PUBLICATIONS

Reff, M. E., "High-level production of recombinant immunoglobu-lins in mammalian cells," *Current Opinion in Biotechnology*, vol. 4, Issue 5, Oct. 1993, pp. 573-576.

Schellenberger et al., "A recombinant polypeptide extends the in vivo half-life of peptides and proteins in a tunable manner," *Nature Biotechnology*, Dec. 2009, vol. 27, No. 12, pp. 1186-1190.

Schier et al., "Isolation of Picomolar Affinity Anti-c-erbB-2 Single-chain Fv by Molecular Evolution of the Complementarity Deter-mining Regions in the Center of the Antibody Binding Site," *Journal of Molecular Biology*, vol. 263, Issue 4, Nov. 8, 1996, pp. 551-567.

Schlapschy, M. et al., "PASylation: a biological alternative to PEGylation for extending the plasma half-life of pharmaceutically active proteins," Protein Engineering, Design and Selection, vol. 26, Issue 8, Aug. 2013, pp. 489-501.

Schodin, B. A. et al., "Binding properties and solubility of single-chain T cell receptors expressed in *E. coli*," *Molecular Immunology*, vol. 33, Issue 9, Jun. 1996, pp. 819-829.

Shalaby et al., "Development of humanized bispecific antibodies reactive with cytotoxic lymphocytes and tumor cells overexpressing the HER2 protooncogene," *Journal of Experimental Medicine*, vol. 175, Issue 1, Jan. 1, 1992, pp. 217-225.

Sinclair, A.M. and Elliott, S., "Glycoengineering: The effect of glycosylation on the properties of therapeutic proteins," *Journal of Pharmaceutical Sciences*, vol. 94, Issue 8, Aug. 2005, pp. 1626-1635.

Torelli and Robotti, "Advance and ADAM: two algorithms for the analysis of global similarity between homologous informational sequences," *Bioinformatics*, vol. 10, Issue 1, Feb. 1994, pp. 3-5, https://doi.org/10.1093/bioinformatics/10.1.3.

Traunecker et al., "Bispecific single chain molecules (Janusins) target cytotoxic lymphocytes on HIV infected cells," *The EMBO Journal*, vol. 10, Issue 12, Dec. 1991, pp. 3655-3659.

Trill et al., "Production of monoclonal antibodies in COS and CHO cells," *Current Opinion in Biotechnology*, vol. 6, Issue 5, 1995, pp. 553-560.

Ward, E.S. et al., "Binding activities of a repertoire of single immunoglobulin variable domains secreted from *Escherichia coli*," *Nature*, vol. 341, Issue 6242, Oct. 1989, pp. 544-546.

Weidanz et al., "Display of functional αß single-chain T-cell recep-tor molecules on the surface of bacteriophage," *Journal of Immu-nological Methods*, vol. 221, Issues 1-2, Dec. 1998, pp. 59-76.

Yuraszeck et al., "Translation and Clinical Development of Bispecific T-cell Engaging Antibodies for Cancer Treatment," *Clinical Phar-macology & Therapeutics*, vol. 101, Issue 5, Cancer Treatment, May 2017, pp. 634-645.

Yaojian, C. et al., "Preparation and preliminary functional study of anti-EGFR/CD3 bispecific antibody," Journal of Fujian Medical University, Issue 6, 2017, pp. 1-13 [Online] [Retrieved on Aug. 26, 2025] Retrieved from the Internet <URL: https://m.fx361.com/news/2017/0309/20473187.html>.

* cited by examiner

Figure 1

Variable domain amino acid sequences of improved UCHT1 variants. CDRs are underlined. Mutations are shown in bold Light chain (v1 (I65A) and v2 (T165A+I202F) SEQ ID NO: 16

AIQMTQSPSSLSASVGDRVTITCRASQDIRNYLNWYQQKPGKAPKLLIYYTSR

LESGVPSRFSGSGSGTDYTLTISSLQPEDFATYYCQQGNTLPWTFGQGTKVEI

K

Heavy chain v1 (T165A) SEQ ID NO: 18

EVQLVESGGGLVQPGGSLRLSCAASGYSFTGYAMNWVRQAPGKGLEWVALINP

YKGVSTYNQKFKDRFTISVDKSKNTAYLQMNSLRAEDTAVYYCARSGYYGDSD

WYFDVWGQGTLVTVSS

Heavy chain v2 (T165A+I202F) SEQ ID NO: 19

EVQLVESGGGLVQPGGSLRLSCAASGYSFTGYAMNWVRQAPGKGLEWVALINP

YKGVSTYNQKFKDRFTFSVDKSKNTAYLQMNSLRAEDTAVYYCARSGYYGDSD

WYFDVWGQGTLVTVSS

Figure 2

Amino acid sequence of a TCR-anti-CD3 fusion protein, incorporating improved UCHT1 scFv variants

Alpha chain SEQ ID NO: 34

MGDAKTTQPNSMESNEEEPVHLPCNHSTISGTDYIHWYRQLPSQGPEYVIHGL
TSNVNNRMASLAIAEDRKSSTLILHRATLRDAAVYYCILILGHSRLGNYIATF
GKGTKLSVIPNIQNPDPAVYQLRDSKSSDKSVCLFTDFDSQTNVSQSKDSDVY
ITDKCVLDMRSMDFKSNSAVAWSNKSDFACANAFNNSIIPEDT

Beta chain v1 (T165A)
Improved UCHT1 scFv is underlined and linkers are shown in italics SEQ ID NO: 32

AIQMTQSPSSLSASVGDRVTITCRASQDIRNYLNWYQQKPGKAPKLLIYYTSR
LESGVPSRFSGSGSGTDYTLTISSLQPEDFATYYCQQGNTLPWTFGQGTKVEI
KGGGGSGGGGSGGGGSGGGGSGGGSEVQLVESGGGLVQPGGSLRLSCAASGYS
FTGYAMNWVRQAPGKGLEWVALINPYKGVSTYNQKFKDRFTISVDKSKNTAYL
QMNSLRAEDTAVYYCARSGYYGDSDWYFDVWGQGTLVTVSSGGGGSDGGITQS
PKYLFRKEGQNVTLSCEQNLNHDAMYWYRQDPGQGLRLIYYSQIMGDEQKGDI
AEGYSVSREKKESFPLTVTSAQKNPTAFYLCASSWWTGGSAFIRFGPGTRLTV
TEDLKNVFPPEVAVFEPSEAEISHTQKATLVCLATGFYPDHVELSWWVNGKEV
HSGVCTDPQPLKEQPALNDSRYALSSRLRVSATFWQDPRNHFRCQVQFYGLSE
NDEWTQDRAKPVTQIVSAEAWGRAD

Beta chain v2 (T165A+I202F)
Improved UCHT1 scFv is underlined and linkers are shown in italics SEQ ID NO: 33

AIQMTQSPSSLSASVGDRVTITCRASQDIRNYLNWYQQKPGKAPKLLIYYTSR
LESGVPSRFSGSGSGTDYTLTISSLQPEDFATYYCQQGNTLPWTFGQGTKVEI
KGGGGSGGGGSGGGGSGGGGSGGGSEVQLVESGGGLVQPGGSLRLSCAASGYS
FTGYAMNWVRQAPGKGLEWVALINPYKGVSTYNQKFKLRFFSVDKSKNTAYL
QMNSLRAEDTAVYYCARSGYYGDSDWYFDVWGQGTLVTVSSGGGGSDGGITQS
PKYLFRKEGQNVTLSCEQNLNHDAMYWYRQDPGQGLRLIYYSQIMGDEQKGDI

AEGYSVSREKKESFPLTVTSAQKNPTAFYLCASSWWTGGSAPIRFGPGTRLTV

TEDLKNVFPPEVAVFEPSEAEISHTQKATLVCLATGFYPDHVELSWWVNGKEV

HSGVCTDPQPLKEQPALNDSRYALSSRLRVSATFWQDPRNHFRCQVQFYGLSE

NDEWTQDRAKPVTQIVSAEAWGRAD SEQ ID NO: 33 cont.

Figure 2 (cont.)

Figure 3
A
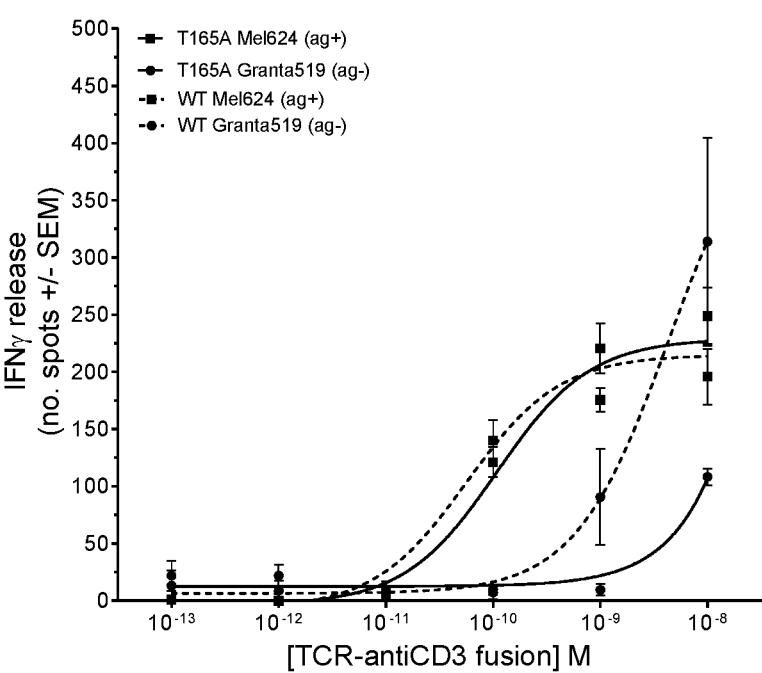
B
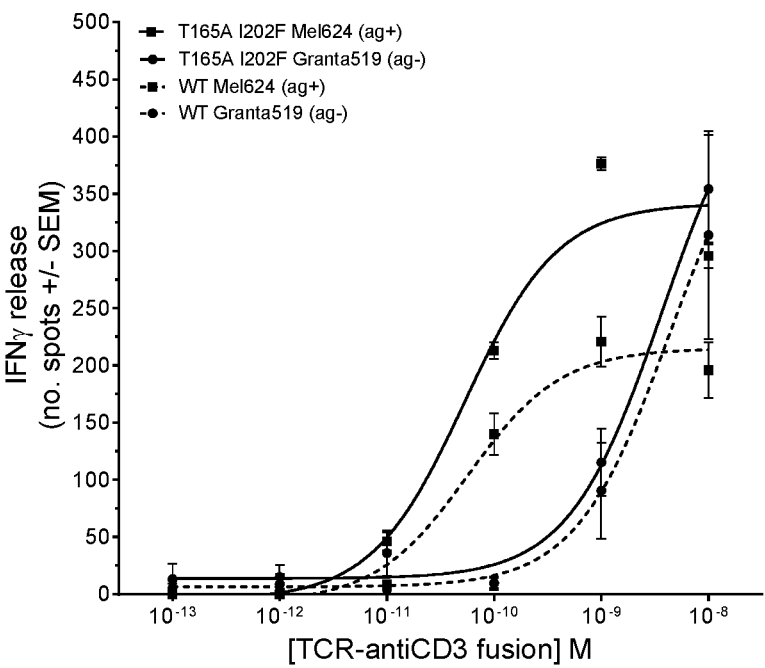

SEQUENCE LISTING

<160> NUMBER OF SEQ ID NOS: 45

<210> SEQ ID NO 1
<211> LENGTH: 6
<212> TYPE: PRT
<213> ORGANISM: Homo sapiens

<400> SEQUENCE: 1

Gln Asp Ile Arg Asn Tyr
1               5

<210> SEQ ID NO 2
<211> LENGTH: 9
<212> TYPE: PRT
<213> ORGANISM: Homo sapiens

<400> SEQUENCE: 2

Gln Gln Gly Asn Thr Leu Pro Trp Thr
1               5

<210> SEQ ID NO 3
<211> LENGTH: 8
<212> TYPE: PRT
<213> ORGANISM: Homo sapiens

<400> SEQUENCE: 3

Gly Tyr Ser Phe Thr Gly Tyr Ala
1               5

<210> SEQ ID NO 4
<211> LENGTH: 8
<212> TYPE: PRT
<213> ORGANISM: Homo sapiens

<400> SEQUENCE: 4

Ile Asn Pro Tyr Lys Gly Val Ser
1               5

<210> SEQ ID NO 5
<211> LENGTH: 15
<212> TYPE: PRT
<213> ORGANISM: Homo sapiens

<400> SEQUENCE: 5

Ala Arg Ser Gly Tyr Tyr Gly Asp Ser Asp Trp Tyr Phe Asp Val
1               5                   10                  15

<210> SEQ ID NO 6
<211> LENGTH: 26
<212> TYPE: PRT
<213> ORGANISM: Homo sapiens

<400> SEQUENCE: 6

Ala Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 7
<211> LENGTH: 26
<212> TYPE: PRT
<213> ORGANISM: Homo sapiens

<400> SEQUENCE: 7

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 8
<211> LENGTH: 17
<212> TYPE: PRT
<213> ORGANISM: Homo sapiens

<400> SEQUENCE: 8

Leu Asn Trp Tyr Gln Gln Lys Pro Gly Lys Ala Pro Lys Leu Leu Ile
1               5                   10                  15

Tyr

<210> SEQ ID NO 9
<211> LENGTH: 36
<212> TYPE: PRT
<213> ORGANISM: Homo sapiens

<400> SEQUENCE: 9

Arg Leu Glu Ser Gly Val Pro Ser Arg Phe Ser Gly Ser Gly Ser Gly
1               5                   10                  15

Thr Asp Tyr Thr Leu Thr Ile Ser Ser Leu Gln Pro Glu Asp Phe Ala
            20                  25                  30

Thr Tyr Tyr Cys
        35

<210> SEQ ID NO 10
<211> LENGTH: 10
<212> TYPE: PRT
<213> ORGANISM: Homo sapiens

<400> SEQUENCE: 10

Phe Gly Gln Gly Thr Lys Val Glu Ile Lys
1               5                   10

<210> SEQ ID NO 11
<211> LENGTH: 25
<212> TYPE: PRT
<213> ORGANISM: Homo sapiens

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 12
<211> LENGTH: 17
<212> TYPE: PRT
<213> ORGANISM: Homo sapiens

<400> SEQUENCE: 12

Met Asn Trp Val Arg Gln Ala Pro Gly Lys Gly Leu Glu Trp Val Ala
1               5                   10                  15

Leu

<210> SEQ ID NO 13
<211> LENGTH: 38
<212> TYPE: PRT
<213> ORGANISM: Homo sapiens
```

-continued

<400> SEQUENCE: 13

Thr Tyr Asn Gln Lys Phe Lys Asp Arg Phe Thr Ile Ser Val Asp Lys
1               5                   10                  15

Ser Lys Asn Thr Ala Tyr Leu Gln Met Asn Ser Leu Arg Ala Glu Asp
            20                  25                  30

Thr Ala Val Tyr Tyr Cys
        35

<210> SEQ ID NO 14
<211> LENGTH: 38
<212> TYPE: PRT
<213> ORGANISM: Homo sapiens

<400> SEQUENCE: 14

Thr Tyr Asn Gln Lys Phe Lys Asp Arg Phe Thr Phe Ser Val Asp Lys
1               5                   10                  15

Ser Lys Asn Thr Ala Tyr Leu Gln Met Asn Ser Leu Arg Ala Glu Asp
            20                  25                  30

Thr Ala Val Tyr Tyr Cys
        35

<210> SEQ ID NO 15
<211> LENGTH: 11
<212> TYPE: PRT
<213> ORGANISM: Homo sapiens

<400> SEQUENCE: 15

Trp Gly Gln Gly Thr Leu Val Thr Val Ser Ser
1               5                   10

<210> SEQ ID NO 16
<211> LENGTH: 107
<212> TYPE: PRT
<213> ORGANISM: Homo sapiens

<400> SEQUENCE: 16

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 17
<211> LENGTH: 107
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

-continued

```
Asp Arg Val Thr Ile Thr Cys Arg Ala Ser Gln Asp Ile Arg Asn Tyr
        20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
        100                 105

<210> SEQ ID NO 18
<211> LENGTH: 122
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
        20                  25                  30

Ala Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
        100                 105                 110

Gly Gln Gly Thr Leu Val Thr Val Ser Ser
        115                 120

<210> SEQ ID NO 19
<211> LENGTH: 122
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
        20                  25                  30

Ala Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Phe Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
        100                 105                 110
```

```
Gly Gln Gly Thr Leu Val Thr Val Ser Ser
        115                 120

<210> SEQ ID NO 20
<211> LENGTH: 253
<212> TYPE: PRT
<213> ORGANISM: Homo sapiens

<400> SEQUENCE: 20

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser
                245                 250

<210> SEQ ID NO 21
<211> LENGTH: 253
<212> TYPE: PRT
<213> ORGANISM: Homo sapiens

<400> SEQUENCE: 21

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60
```

-continued

```
Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
                180                 185                 190

Gln Lys Phe Lys Asp Arg Phe Thr Phe Ser Val Asp Lys Ser Lys Asn
            195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser
                245                 250
```

```
<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 22

Gly Gly Gly Ser Gly Gly Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 23

Gly Gly Gly Gly Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence
```

-continued

<400> SEQUENCE: 24

Gly Gly Gly Ser Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 25

Gly Gly Ser Gly Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 26

Gly Ser Gly Gly Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 27

Gly Ser Gly Gly Gly Pro
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 28

Gly Gly Glu Pro Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: Linker sequence

<400> SEQUENCE: 29

Gly Gly Glu Gly Gly Gly Pro
1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 30

Gly Gly Glu Gly Gly Gly Ser Glu Gly Gly Gly Ser
1               5                   10

<210> SEQ ID NO 31
<211> LENGTH: 244
<212> TYPE: PRT
<213> ORGANISM: Homo sapiens

<400> SEQUENCE: 31

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Met Gly Asp Glu Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Trp Trp
                85                  90                  95

Thr Gly Gly Ser Ala Pro Ile Arg Phe Gly Pro Gly Thr Arg Leu Thr
            100                 105                 110

Val Thr Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asp Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp

-continued

```
<210> SEQ ID NO 32
<211> LENGTH: 502
<212> TYPE: PRT
<213> ORGANISM: Homo sapiens

<400> SEQUENCE: 32

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Asp Gly Gly Ile Thr Gln Ser Pro Lys Tyr Leu Phe Arg Lys
            260                 265                 270

Glu Gly Gln Asn Val Thr Leu Ser Cys Glu Gln Asn Leu Asn His Asp
        275                 280                 285

Ala Met Tyr Trp Tyr Arg Gln Asp Pro Gly Gln Gly Leu Arg Leu Ile
    290                 295                 300

Tyr Tyr Ser Gln Ile Met Gly Asp Glu Gln Lys Gly Asp Ile Ala Glu
305                 310                 315                 320

Gly Tyr Ser Val Ser Arg Glu Lys Lys Glu Ser Phe Pro Leu Thr Val
                325                 330                 335

Thr Ser Ala Gln Lys Asn Pro Thr Ala Phe Tyr Leu Cys Ala Ser Ser
            340                 345                 350

Trp Trp Thr Gly Gly Ser Ala Pro Ile Arg Phe Gly Pro Gly Thr Arg
        355                 360                 365

Leu Thr Val Thr Glu Asp Leu Lys Asn Val Phe Pro Pro Glu Val Ala
    370                 375                 380
```

-continued

```
Val Phe Glu Pro Ser Glu Ala Glu Ile Ser His Thr Gln Lys Ala Thr
385                 390                 395                 400

Leu Val Cys Leu Ala Thr Gly Phe Tyr Pro Asp His Val Glu Leu Ser
            405                 410                 415

Trp Trp Val Asn Gly Lys Glu Val His Ser Gly Val Cys Thr Asp Pro
            420                 425                 430

Gln Pro Leu Lys Glu Gln Pro Ala Leu Asn Asp Ser Arg Tyr Ala Leu
        435                 440                 445

Ser Ser Arg Leu Arg Val Ser Ala Thr Phe Trp Gln Asp Pro Arg Asn
    450                 455                 460

His Phe Arg Cys Gln Val Gln Phe Tyr Gly Leu Ser Glu Asn Asp Glu
465                 470                 475                 480

Trp Thr Gln Asp Arg Ala Lys Pro Val Thr Gln Ile Val Ser Ala Glu
                485                 490                 495

Ala Trp Gly Arg Ala Asp
                500

<210> SEQ ID NO 33
<211> LENGTH: 502
<212> TYPE: PRT
<213> ORGANISM: Homo sapiens

<400> SEQUENCE: 33

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Phe Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255
```

-continued

```
Gly Ser Asp Gly Gly Ile Thr Gln Ser Pro Lys Tyr Leu Phe Arg Lys
            260                 265                 270

Glu Gly Gln Asn Val Thr Leu Ser Cys Glu Gln Asn Leu Asn His Asp
            275                 280                 285

Ala Met Tyr Trp Tyr Arg Gln Asp Pro Gly Gln Gly Leu Arg Leu Ile
            290                 295                 300

Tyr Tyr Ser Gln Ile Met Gly Asp Glu Gln Lys Gly Asp Ile Ala Glu
305                 310                 315                 320

Gly Tyr Ser Val Ser Arg Glu Lys Lys Glu Ser Phe Pro Leu Thr Val
            325                 330                 335

Thr Ser Ala Gln Lys Asn Pro Thr Ala Phe Tyr Leu Cys Ala Ser Ser
            340                 345                 350

Trp Trp Thr Gly Gly Ser Ala Pro Ile Arg Phe Gly Pro Gly Thr Arg
            355                 360                 365

Leu Thr Val Thr Glu Asp Leu Lys Asn Val Phe Pro Pro Glu Val Ala
            370                 375                 380

Val Phe Glu Pro Ser Glu Ala Glu Ile Ser His Thr Gln Lys Ala Thr
385                 390                 395                 400

Leu Val Cys Leu Ala Thr Gly Phe Tyr Pro Asp His Val Glu Leu Ser
            405                 410                 415

Trp Trp Val Asn Gly Lys Glu Val His Ser Gly Val Cys Thr Asp Pro
            420                 425                 430

Gln Pro Leu Lys Glu Gln Pro Ala Leu Asn Asp Ser Arg Tyr Ala Leu
            435                 440                 445

Ser Ser Arg Leu Arg Val Ser Ala Thr Phe Trp Gln Asp Pro Arg Asn
            450                 455                 460

His Phe Arg Cys Gln Val Gln Phe Tyr Gly Leu Ser Glu Asn Asp Glu
465                 470                 475                 480

Trp Thr Gln Asp Arg Ala Lys Pro Val Thr Gln Ile Val Ser Ala Glu
            485                 490                 495

Ala Trp Gly Arg Ala Asp
            500

<210> SEQ ID NO 34
<211> LENGTH: 202
<212> TYPE: PRT
<213> ORGANISM: Homo sapiens

<400> SEQUENCE: 34

Met Gly Asp Ala Lys Thr Thr Gln Pro Asn Ser Met Glu Ser Asn Glu
1               5                   10                  15

Glu Glu Pro Val His Leu Pro Cys Asn His Ser Thr Ile Ser Gly Thr
            20                  25                  30

Asp Tyr Ile His Trp Tyr Arg Gln Leu Pro Ser Gln Gly Pro Glu Tyr
            35                  40                  45

Val Ile His Gly Leu Thr Ser Asn Val Asn Asn Arg Met Ala Ser Leu
        50                  55                  60

Ala Ile Ala Glu Asp Arg Lys Ser Ser Thr Leu Ile Leu His Arg Ala
65                  70                  75                  80

Thr Leu Arg Asp Ala Ala Val Tyr Tyr Cys Ile Leu Ile Leu Gly His
                85                  90                  95

Ser Arg Leu Gly Asn Tyr Ile Ala Thr Phe Gly Lys Gly Thr Lys Leu
            100                 105                 110

Ser Val Ile Pro Asn Ile Gln Asn Pro Asp Pro Ala Val Tyr Gln Leu
```

-continued

```
              115                 120                 125
Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Cys Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr
            195                 200

<210> SEQ ID NO 35
<211> LENGTH: 502
<212> TYPE: PRT
<213> ORGANISM: Homo sapiens

<400> SEQUENCE: 35

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Asp Gly Gly Ile Thr Gln Ser Pro Lys Tyr Leu Phe Arg Lys
            260                 265                 270

Glu Gly Gln Asn Val Thr Leu Ser Cys Glu Gln Asn Leu Asn His Asp
            275                 280                 285
```

-continued

```
Ala Met Tyr Trp Tyr Arg Gln Asp Pro Gly Gln Gly Leu Arg Leu Ile
    290                 295                 300

Tyr Tyr Ser Gln Ile Met Gly Asp Glu Gln Lys Gly Asp Ile Ala Glu
305                 310                 315                 320

Gly Tyr Ser Val Ser Arg Glu Lys Lys Glu Ser Phe Pro Leu Thr Val
                325                 330                 335

Thr Ser Ala Gln Lys Asn Pro Thr Ala Phe Tyr Leu Cys Ala Ser Ser
                340                 345                 350

Trp Trp Thr Gly Gly Ser Ala Pro Ile Arg Phe Gly Pro Gly Thr Arg
                355                 360                 365

Leu Thr Val Thr Glu Asp Leu Lys Asn Val Phe Pro Pro Glu Val Ala
    370                 375                 380

Val Phe Glu Pro Ser Glu Ala Glu Ile Ser His Thr Gln Lys Ala Thr
385                 390                 395                 400

Leu Val Cys Leu Ala Thr Gly Phe Tyr Pro Asp His Val Glu Leu Ser
                405                 410                 415

Trp Trp Val Asn Gly Lys Glu Val His Ser Gly Val Cys Thr Asp Pro
                420                 425                 430

Gln Pro Leu Lys Glu Gln Pro Ala Leu Asn Asp Ser Arg Tyr Ala Leu
                435                 440                 445

Ser Ser Arg Leu Arg Val Ser Ala Thr Phe Trp Gln Asp Pro Arg Asn
    450                 455                 460

His Phe Arg Cys Gln Val Gln Phe Tyr Gly Leu Ser Glu Asn Asp Glu
465                 470                 475                 480

Trp Thr Gln Asp Arg Ala Lys Pro Val Thr Gln Ile Val Ser Ala Glu
                485                 490                 495

Ala Trp Gly Arg Ala Asp
                500

<210> SEQ ID NO 36
<211> LENGTH: 502
<212> TYPE: PRT
<213> ORGANISM: Homo sapiens

<400> SEQUENCE: 36

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160
```

```
Thr Gly Tyr Ala Met Asn Trp Val Arg Gln Ala Pro Gly Lys Gly Leu
            165             170             175

Glu Trp Val Ala Leu Ile Asn Pro Tyr Lys Gly Val Ser Thr Tyr Asn
            180             185             190

Gln Lys Phe Lys Asp Arg Phe Thr Phe Ser Val Asp Lys Ser Lys Asn
            195             200             205

Thr Ala Tyr Leu Gln Met Asn Ser Leu Arg Ala Glu Asp Thr Ala Val
        210             215             220

Tyr Tyr Cys Ala Arg Ser Gly Tyr Tyr Gly Asp Ser Asp Trp Tyr Phe
225             230             235             240

Asp Val Trp Gly Gln Gly Thr Leu Val Thr Val Ser Ser Gly Gly Gly
            245             250             255

Gly Ser Asp Gly Gly Ile Thr Gln Ser Pro Lys Tyr Leu Phe Arg Lys
            260             265             270

Glu Gly Gln Asn Val Thr Leu Ser Cys Glu Gln Asn Leu Asn His Asp
            275             280             285

Ala Met Tyr Trp Tyr Arg Gln Asp Pro Gly Gln Gly Leu Arg Leu Ile
        290             295             300

Tyr Tyr Ser Gln Ile Met Gly Asp Glu Gln Lys Gly Asp Ile Ala Glu
305             310             315             320

Gly Tyr Ser Val Ser Arg Glu Lys Lys Glu Ser Phe Pro Leu Thr Val
            325             330             335

Thr Ser Ala Gln Lys Asn Pro Thr Ala Phe Tyr Leu Cys Ala Ser Ser
            340             345             350

Trp Trp Thr Gly Gly Ser Ala Pro Ile Arg Phe Gly Pro Gly Thr Arg
            355             360             365

Leu Thr Val Thr Glu Asp Leu Lys Asn Val Phe Pro Pro Glu Val Ala
        370             375             380

Val Phe Glu Pro Ser Glu Ala Glu Ile Ser His Thr Gln Lys Ala Thr
385             390             395             400

Leu Val Cys Leu Ala Thr Gly Phe Tyr Pro Asp His Val Glu Leu Ser
            405             410             415

Trp Trp Val Asn Gly Lys Glu Val His Ser Gly Val Cys Thr Asp Pro
            420             425             430

Gln Pro Leu Lys Glu Gln Pro Ala Leu Asn Asp Ser Arg Tyr Ala Leu
            435             440             445

Ser Ser Arg Leu Arg Val Ser Ala Thr Phe Trp Gln Asp Pro Arg Asn
        450             455             460

His Phe Arg Cys Gln Val Gln Phe Tyr Gly Leu Ser Glu Asn Asp Glu
465             470             475             480

Trp Thr Gln Asp Arg Ala Lys Pro Val Thr Gln Ile Val Ser Ala Glu
            485             490             495

Ala Trp Gly Arg Ala Asp
            500
```

```
<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence
<220> FEATURE:
<223> OTHER INFORMATION: See specification as filed for detailed
```

-continued description of substitutions and preferred embodiments

<400> SEQUENCE: 37

Gly Gly Gly Gly Ser
1               5

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 39
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Ala Met Asn Trp Val Arg Gln Ala Pro Gly Lys Gly Leu Glu Trp Val
            35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 40
<211> LENGTH: 122
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Ala Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Phe Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
            115                 120

<210> SEQ ID NO 41
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gly Asp Ala Lys Thr Thr Gln Pro Asn Ser Met Glu Ser Asn Glu
1               5                   10                  15

Glu Glu Pro Val His Leu Pro Cys Asn His Ser Thr Ile Ser Gly Thr
            20                  25                  30

Asp Tyr Ile His Trp Tyr Arg Gln Leu Pro Ser Gln Gly Pro Glu Tyr
            35                  40                  45

Val Ile His Gly Leu Thr Ser Asn Val Asn Asn Arg Met Ala Ser Leu
    50                  55                  60

Ala Ile Ala Glu Asp Arg Lys Ser Ser Thr Leu Ile Leu His Arg Ala
65                  70                  75                  80

Thr Leu Arg Asp Ala Ala Val Tyr Tyr Cys Ile Leu Ile Leu Gly His
                85                  90                  95

Ser Arg Leu Gly Asn Tyr Ile Ala Thr Phe Gly Lys Gly Thr Lys Leu
            100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Cys Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr
            195                 200
```

```
<210> SEQ ID NO 42
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
            245                 250                 255

Gly Ser Asp Gly Gly Ile Thr Gln Ser Pro Lys Tyr Leu Phe Arg Lys
            260                 265                 270

Glu Gly Gln Asn Val Thr Leu Ser Cys Glu Gln Asn Leu Asn His Asp
        275                 280                 285

Ala Met Tyr Trp Tyr Arg Gln Asp Pro Gly Gln Gly Leu Arg Leu Ile
    290                 295                 300

Tyr Tyr Ser Gln Ile Met Gly Asp Glu Gln Lys Gly Asp Ile Ala Glu
305                 310                 315                 320

Gly Tyr Ser Val Ser Arg Glu Lys Lys Glu Ser Phe Pro Leu Thr Val
            325                 330                 335

Thr Ser Ala Gln Lys Asn Pro Thr Ala Phe Tyr Leu Cys Ala Ser Ser
        340                 345                 350

Trp Trp Thr Gly Gly Ser Ala Pro Ile Arg Phe Gly Pro Gly Thr Arg
```

-continued

```
                355                 360                 365

Leu Thr Val Thr Glu Asp Leu Lys Asn Val Phe Pro Pro Glu Val Ala
    370                 375                 380

Val Phe Glu Pro Ser Glu Ala Glu Ile Ser His Thr Gln Lys Ala Thr
385                 390                 395                 400

Leu Val Cys Leu Ala Thr Gly Phe Tyr Pro Asp His Val Glu Leu Ser
                405                 410                 415

Trp Trp Val Asn Gly Lys Glu Val His Ser Gly Val Cys Thr Asp Pro
                420                 425                 430

Gln Pro Leu Lys Glu Gln Pro Ala Leu Asn Asp Ser Arg Tyr Ala Leu
            435                 440                 445

Ser Ser Arg Leu Arg Val Ser Ala Thr Phe Trp Gln Asp Pro Arg Asn
    450                 455                 460

His Phe Arg Cys Gln Val Gln Phe Tyr Gly Leu Ser Glu Asn Asp Glu
465                 470                 475                 480

Trp Thr Gln Asp Arg Ala Lys Pro Val Thr Gln Ile Val Ser Ala Glu
                485                 490                 495

Ala Trp Gly Arg Ala Asp
                500

<210> SEQ ID NO 43
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Gly Gly Gly Gly Ser Gly
            115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
                180                 185                 190

Gln Lys Phe Lys Asp Arg Phe Thr Phe Ser Val Asp Lys Ser Lys Asn
            195                 200                 205
```

-continued

```
Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Asp Gly Gly Ile Thr Gln Ser Pro Lys Tyr Leu Phe Arg Lys
                260                 265                 270

Glu Gly Gln Asn Val Thr Leu Ser Cys Glu Gln Asn Leu Asn His Asp
            275                 280                 285

Ala Met Tyr Trp Tyr Arg Gln Asp Pro Gly Gln Gly Leu Arg Leu Ile
    290                 295                 300

Tyr Tyr Ser Gln Ile Met Gly Asp Glu Gln Lys Gly Asp Ile Ala Glu
305                 310                 315                 320

Gly Tyr Ser Val Ser Arg Glu Lys Lys Glu Ser Phe Pro Leu Thr Val
                325                 330                 335

Thr Ser Ala Gln Lys Asn Pro Thr Ala Phe Tyr Leu Cys Ala Ser Ser
            340                 345                 350

Trp Trp Thr Gly Gly Ser Ala Pro Ile Arg Phe Gly Pro Gly Thr Arg
            355                 360                 365

Leu Thr Val Thr Glu Asp Leu Lys Asn Val Phe Pro Pro Glu Val Ala
    370                 375                 380

Val Phe Glu Pro Ser Glu Ala Glu Ile Ser His Thr Gln Lys Ala Thr
385                 390                 395                 400

Leu Val Cys Leu Ala Thr Gly Phe Tyr Pro Asp His Val Glu Leu Ser
                405                 410                 415

Trp Trp Val Asn Gly Lys Glu Val His Ser Gly Val Cys Thr Asp Pro
            420                 425                 430

Gln Pro Leu Lys Glu Gln Pro Ala Leu Asn Asp Ser Arg Tyr Ala Leu
            435                 440                 445

Ser Ser Arg Leu Arg Val Ser Ala Thr Phe Trp Gln Asp Pro Arg Asn
    450                 455                 460

His Phe Arg Cys Gln Val Gln Phe Tyr Gly Leu Ser Glu Asn Asp Glu
465                 470                 475                 480

Trp Thr Gln Asp Arg Ala Lys Pro Val Thr Gln Ile Val Ser Ala Glu
                485                 490                 495

Ala Trp Gly Arg Ala Asp
                500
```

```
<210> SEQ ID NO 44
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60
```

-continued

```
Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
            115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
                180                 185                 190

Gln Lys Phe Lys Asp Arg Phe Thr Ile Ser Val Asp Lys Ser Lys Asn
            195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser
                245                 250
```

```
<210> SEQ ID NO 45
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
            115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Ala Met Asn Trp Val Arg Gln Ala Pro Gly Lys Gly Leu
```

-continued

```
            165                 170                 175
Glu Trp Val Ala Leu Ile Asn Pro Tyr Lys Gly Val Ser Thr Tyr Asn
            180                 185                 190

Gln Lys Phe Lys Asp Arg Phe Thr Phe Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser
                245                 250
```

CD3-SPECIFIC BINDING MOLECULES

SEQUENCE LISTING

The instant application contains a Sequence Listing which has been submitted electronically in ASCII format and is hereby incorporated by reference in its entirety. Said ASCII copy, created on Apr. 25, 2025, is named 49574US_CRF_sequencelisting.txt and is 27,896 bytes in size.

FIELD OF INVENTION

The present invention relates to specific binding molecules which bind to CD3, particularly antibodies and fragments thereof, with improved properties.

BACKGROUND TO THE INVENTION

CD3 (cluster of differentiation 3) is a T cell co-receptor which helps to activate both the cytotoxic T cell (CD8+ T cells) and also T helper cells (CD4+ T cells). CD3 associates with the T-cell receptor (TCR) and the ζ-chain (zeta-chain; CD247) to generate an activation signal in T lymphocytes. The TCR, ζ-chain, and CD3 molecules together constitute the TCR complex.

Antibodies which bind to CD3 are known and have utility as immunosuppressive drugs Examples include muromonab-CD3 (Janssen-Cilag), otelixizumab (also known as TRX4), teplizumab (also known as PRV-031), and visilizumab.

Anti-CD3 antibodies also have utility as T cell recruiting agents in a class of protein based therapeutics broadly known as T cell engaging bispecifics (Baeuerle et al., Cancer Res. 2009 Jun. 15; 69(12):4941-4). Such therapeutics combine a target cell recognition domain with an anti-CD3 domain. Simultaneous engagement of target cells (e.g. a cancer cell) and CD3+ cytotoxic T cells leads to activation of CD3 signalling pathways, independently of T cell receptor specificity, and ultimately results in target cell death. The bispecific antibody blinatumomab (Amgen) is an example of marketed T cell engaging therapeutic for the treatment of acute lymphoblastic leukemia (ALL) A number of further T cell engaging bispecifics are being investigated in clinical trials for the treatment of various cancers and infectious diseases (for example see tables provided in Yuraszeck et al, Clin Pharmacol Ther 2017 May; 101(5):634-645, and Husain et al., BioDrugs. 2018 October; 32(5):441-464).

The majority of T cell engaging bispecifics recognise cell surface antigens on the target cell. In addition, T cell engaging bispecifics are also known that recognises short peptides derived from intracellular antigens and presented on the cell surface in complex with MHC (pMHC) (Liddy et al., Nat Med. 2012 June; 18(6):980-7).

The antibody UCHT1 is a clinically relevant anti-CD3 antibody that is known in the art (Shalaby et al., J Exp Med. 1992 Jan. 1; 175(1):217-25; U.S. Pat. No. 5,821,337). An scFv fragment of a humanised UCHT1 antibody has been fused to a soluble T cell receptor to construct a T cell engaging bispecific that binds to pMHC on a target cell (for example see WO2011001152).

DESCRIPTION OF THE INVENTION

The present inventors have, surprisingly, found that introduction of certain mutations in the amino acid sequence of UCHT1 leads to the generation of T cell engaging bispecific molecules with unexpected properties that are particularly beneficial for clinical use.

In a first aspect, there is provided a specific binding molecule which binds to CD3 and comprises a polypeptide having an immunoglobulin VL domain and an immunoglobulin VH domain in which the VL domain comprises Complementarity Determining Regions (CDRs) VLCDR1, VLCDR2 and VLCDR3, and in which the VH domain comprises Complementarity Determining Regions (CDRs) VHCDR1, VHCDR2, VHCDR3, each having a respective amino acid sequence as follows in which

| | (SEQ ID NO: 1) |
|---|---|
| VLCDR1 is QDIRNY | |
| VLCDR2 is YTS | |
| | (SEQ ID NO: 2) |
| VLCDR3 is QQGNTLPWT | |
| | (SEQ ID NO: 3) |
| VHCDR1 is GYSFTGYA | |
| | (SEQ ID NO: 4) |
| VHCDR2 is INPYKGVS | |
| | (SEQ ID NO: 5) |
| VHCDR3 is ARSGYYGDSDWYFDV | | or an amino acid sequence at least 70% identical thereto.

CDRs are defined according to the international ImMunoGeneTics information system (IMGT®) (LeFranc et al., Nucleic Acids Res. 2009 January; 37(Database issue): D1006-12)

In particular, the specific binding molecules of the invention comprise an alanine at the C-terminal end of VHCDR1, corresponding to position 38 in IMGT® numbering, (which is designated position 165 herein, and is exemplified and shown in bold in the heavy chain sequence v1 of FIG. 1). It has been found that molecules including this mutation have improved properties, including an improved specificity window compared to molecules without this mutation.

The CDRs may be provided in an antibody variable domain framework sequence. The framework sequence may be a mouse framework sequence or a human framework sequence or a humanised framework sequence or any other suitable framework. Preferable the framework is a human or humanised framework sequence. Human or humanised frameworks have substantially the amino acid sequence of a human immunoglobulin. In certain cases, mouse frameworks, human frameworks and humanised frameworks may be mixed in any combination.

Preferably, the immunoglobulin VL comprises an overall sequence VLFW1-VLCDR1-VLFW2-VLCDR2-VLFW3-VLCDR3-VLFW4, wherein VLFW1, VLFW2, VLFW3, and VLFW4 are VL framework (VLFW) sequences 1 to 4 respectively the immunoglobulin VH comprises an overall sequence VHFW1-VHCDR1-VHFW2-VHCDR2-VHFW3-VHCDR3-VHFW4, wherein VHFW1, VHFW2, VHFW3, and VHFW4 are VH framework (VHFW) sequences 1 to 4 respectively, optionally wherein the VLFW and VHFW sequences are mouse, human, or humanised framework sequences.

Preferably, the immunoglobulin VL comprises an overall sequence as follows: VLFW1-VLCDR1-VLFW2-VLCDR2-VLFW3-VLCDR3-VLFW4, wherein VLFW1, VLFW2, VLFW3, and VLFW4 are framework (FW)

sequences 1 to 4 respectively, VLFW1, VLFW2, VLFW3, and VLFW4 each having a respective amino acid sequence as follows in which.

```
                              (SEQ ID NO: 6)
VLFW1 is AIQMTQSPSSLSASVGDRVTITCRAS
or (SEQ ID NO: 7)
DIQMTQSPSSLSASVGDRVTITCRAS (SEQ ID NO: 8)
VLFW2 is LNWYQQKPGKAPKLLIY (SEQ ID NO: 9)
VLFW3 is RLESGVPSRFSGSGSGTDYTLTISSLQPEDFATYYC (SEQ ID NO: 10)
VLFW4 is FGQGTKVEIK
``` or an amino acid sequence at least 70% identical thereto.

Preferably, the immunoglobulin VH comprises an overall sequence as follows: VHFW1-VHCDR1-VHFW2-VHCDR2-VHFW3-VHCDR3-VHFW4, wherein VHFW1, VHFW2, VHFW3, and VHFW4 are framework (FW) sequences 1 to 4 respectively, VHFW1, VHFW2, VHFW3, and VHFW4 each having a respective amino acid sequence as follows in which:

```
                              (SEQ ID NO: 11)
VHFW1 is EVQLVESGGGLVQPGGSLRLSCAAS (SEQ ID NO: 12)
VHFW2 is MNWVRQAPGKGLEWVAL (SEQ ID NO: 13)
VHFW3 is TYNQKFKDRFTISVDKSKNTAYLQMNSLRAEDTAVYYC
or (SEQ ID NO: 14)
TYNQKFKDRFTFSVDKSKNTAYLQMNSLRAEDTAVYYC (SEQ ID NO: 15)
VHFW4 is WGQGTLVTVSS
``` or an amino acid sequence at least 70% identical thereto.

In particular, the specific binding molecules of the invention comprise phenylalanine in VHFW3 in the position corresponding to position 78 in IMGT® numbering, (which is designated position 202 herein, and is exemplified and shown in bold in the heavy chain sequence v2 of FIG. 1). It has been found that molecules including this mutation in addition to alanine at position 38 have increased efficiency of T cell activation compared to molecules without these mutations.

Preferably the immunoglobin VL comprises the sequence:

```
                              (SEQ ID NO: 16)
AIQMTQSPSSLSASVGDRVTITCRASQDIRNYLNWYQQKPGKAPKLLIYY

TSRLESGVPSRFSGSGSGTDYTLTISSLQPEDFATYYCQQGNTLPWTFGQ

GTKVEIK;
or (SEQ ID NO: 17)
DIQMTQSPSSLSASVGDRVTITCRASQDIRNYLNWYQQKPGKAPKLLIYY

TSRLESGVPSRFSGSGSGTDYTLTISSLQPEDFATYYCQQGNTLPWTFGQ

GTKVEIK
``` or an amino acid sequence at least 70% identical thereto.

Preferably the immunoglobin VH comprises the sequence.

```
                              (SEQ ID NO: 18)
EVQLVESGGGLVQPGGSLRLSCAASGYSFTGYAMNWVRQAPGKGLEWVAL

INPYKGVSTYNQKFKDRFTISVDKSKNTAYLQMNSLRAEDTAVYYCARSG

YYGDSDWYFDVWGQGTLVTVSS;
or (SEQ ID NO: 19)
EVQLVESGGGLVQPGGSLRLSCAASGYSFTGYAMNWVRQAPGKGLEWVAL

INPYKGVSTYNQKFKDRFTFSVDKSKNTAYLQMNSLRAEDTAVYYCARSG

YYGDSDWYFDVWGQGTLVTVSS
``` or an amino acid sequence at least 70% identical thereto.

Preferably, the specific binding molecule is in the form of a scFv fragment.

Preferably, the immunoglobin VL and VH domains are connected via linker. The linker may be any amino acid sequence, preferably 5, 6, 7, 8, 9, 10, 11, 12, 13, 14, 15, 16, 17, 18, 19, 20, 21, 22, 23, 24, 25, 26, 27, 28, 29 or 30 amino acids in length. A preferred linker includes a sequence with the formula (GGGGS), (SEQ ID NO: 23), optionally in addition to other amino acids. Accordingly, there is provided a single chain specific binding molecule having the sequence:

```
                              (SEQ ID NO: 20)
AIQMTQSPSSLSASVGDRVTITCRASQDIRNYLNWYQQKPGKAPKLLIYY

TSRLESGVPSRFSGSGSGTDYTLTISSLQPEDFATYYCQQGNTLPWTFGQ

GTKVEIKGGGGSGGGGSGGGGSGGGGSGGGGSEVQLVESGGGLVQPGGSLR

LSCAASGYSFTGYAMNWVRQAPGKGLEWVALINPYKGVSTYNQKFKDRFT

ISVDKSKNTAYLQMNSLRAEDTAVYYCARSGYYGDSDWYFDVWGQGTLVT

VSS;
or (SEQ ID NO: 21)
AIQMTQSPSSLSASVGDRVTITCRASQDIRNYLNWYQQKPGKAPKLLIYY

TSRLESGVPSRFSGSGSGTDYTLTISSLQPEDFATYYCQQGNTLPWTFGQ

GTKVEIKGGGGSGGGGSGGGGSGGGGSGGGGSEVQLVESGGGLVQPGGSLR

LSCAASGYSFTGYAMNWVRQAPGKGLEWVALINPYKGVSTYNQKFKDRFT

FSVDKSKNTAYLQMNSLRAEDTAVYYCARSGYYGDSDWYFDVWGQGTLVT

VSS
``` or an amino acid sequence at least 70% identical thereto.

The specific binding molecule may also be part of a fusion protein comprising further domains. Fusion proteins may be constructed via N-terminal or C-terminal fusion to either the VL or VH immunoglobin domains. Further domains may be fused via linkers. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. The linker may be any amino acid sequence, preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers include, but are not limited to: GGGSGGGG (SEQ ID NO: 22), GGGGS (SEQ ID NO:23)$_a$ GGGSG (SEQ ID NO: 24), GGSGG (SEQ ID NO: 25), GSGGG (SEQ ID NO: 26), GSGGGP (SEQ ID NO. 27), GGEPS (SEQ ID NO. 28), GGEGGGP (SEQ ID NO: 29), and GGEGGGSEGGGS (SEQ ID NO: 30) (as described in WO2010/133828). A preferred linker includes a sequence with the formula (GGGGS)$_n$ (SEQ ID NO: 23), optionally in addition to other amino acids.

Preferably, the specific binding molecule shows one or more improved therapeutic properties relative to the non-mutated molecule when used as part of a bispecific molecule, preferably a T cell engaging bispecific as described herein. Preferably, the improved therapeutic properties are selected from an improved therapeutic window and/or an increase in maximum T cell activation at a given concentration. An improved therapeutic window may enable higher dosing while minimising toxicity resulting from off target activation. An increase in maximum T cell activation at a given concentration of bispecific molecule may enable more efficient killing of target cells at a given dose of drug. Methods to determine T cell activation are known in the art and include release of immune activating cytokines and T cell mediated cell death. The therapeutic window for a T cell engaging bispecific may be determined by measuring T cell activation in the presence of antigen positive cells and antigen negative cells and calculating the difference between the two measurements. Further details of preferred methods are described in Example 2.

Preferably the anti-CD3 antibody of the invention binds the CD3 epsilon sub-unit of CD3

Specific binding molecules according to the invention may be used in a method of treatment or diagnosis of the human or animal body, such as a method of treatment of a condition in a patient (preferably human) which comprises administering to said patient an effective amount of a specific binding molecule of the invention. The invention also provides a specific binding molecule of the present invention for use in medicine, as well as the use of a specific binding molecule of the present invention in the manufacture of a medicament for the diagnosis or treatment of a tumour.

These and other aspects of the invention are described in further detail below.

As used herein, "treatment" includes any regime that can benefit a human or non-human animal, preferably mammal. The treatment may be in respect of an existing condition or may be prophylactic (preventative treatment).

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to herein as "mab".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding molecule or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E S. et al., Nature 341:544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., Science 242:423-426 (1988); Huston et al., PNAS USA 85:5879-5883 (1988)); (viii) bispecific single chain Fv dimers (PCT/US92/09965) and (ix) 'diabodies', multivalent or multispecific fragments constructed by gene fusion (WO94/13804; P. Hollinger et al., Proc. Natl. Acad Sci. USA 90: 6444-6448 (1993)).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Hollinger & Winter, Current Opinion Biotechnol. 4:446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10:3655-3659 (1991).

Bispecific diabodies, as opposed to bispecific whole antibodies, may also be useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

"Specific" is generally used to refer to the situation in which one member of a specific binding pair will not show any significant binding to molecules other than its specific binding partner(s), and, e.g., has less than about 30%, preferably 20%, 10%, or 1% cross-reactivity with any other molecule. The term is also applicable where e.g. an antigen binding domain is specific for a particular epitope which is carried by a number of antigens, in which case, the specific binding molecule carrying the antigen binding domain will be able to bind to the various antigens carrying the epitope.

"Isolated" refers to the state in which specific binding molecules of the invention or nucleic acid encoding such binding molecules will preferably be, in accordance with the present invention Molecules and nucleic acid will generally be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Specific binding molecules and nucleic acid may be formulated with diluents or adjuvants and still for practical purposes be isolated—for example, the molecules will normally be mixed with gelatin or other carriers if used to coat microtitre plates for use in immunoassays, or will be mixed with pharmaceutically acceptable carriers or diluents when used in diagnosis or therapy Specific binding molecules may be glycosylated, either naturally or by systems of heterologous eukaryotic cells, or they may be (for example if produced by expression in a prokaryotic cell) unglycosylated.

By "substantially as set out" it is meant that the CDR regions of the invention will be either identical or highly homologous to the specified regions of FIGS. 1*a* and 1*cb*. By "highly homologous" it is contemplated that from 1 to 5, from 1 to 4, from 1 to 3, 2 or 1 substitutions may be made in the CDRs.

The invention also includes within its scope polypeptides having the amino acid sequence as set out in FIGS. 1 and 2 and sequences having substantial identity thereto, for example, at least 70%, at least 80%, at least 85%, at least 90%, at least 95% or 99% identity thereto.

The variable domains may be derived from any germline or rearranged human variable domain, or may be a synthetic variable domain based on consensus sequences of known human variable domains. The sequences of the invention may be introduced into a repertoire of variable domains lacking CDR3 regions, using recombinant DNA technology, such as the shuffling or combinatorial techniques disclosed by Stemmer (Nature 370:389-391 (1994)) who describes the technique in relation to a beta-lactamase gene but observes that the approach may be used for the generation of antibodies.

A further alternative is to generate novel VH or VL regions carrying the sequences of the invention using random mutagenesis of, for example, the SC104 VH or VL genes to generate mutations within the entire variable domain. Such a technique is described by Gram et al (Proc. Natl. Acad Sci. USA 89:3576-3580 (1992)), who used error-prone PCR.

Another method which may be used is to direct mutagenesis to CDR regions of VH or VL genes. Such techniques are disclosed by Barbas et al (Proc. Natl Acad Sci. USA 91:3809-3813 (1994)) and Schier et al (J. Mol. Biol 263: 551-567 (1996)).

A substantial portion of an immunoglobulin variable domain will generally comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding molecules of the present invention made by recombinant DNA techniques may result in the introduction of N- or C-terminal residues encoded by linkers introduced to facilitate cloning or other manipulation steps, including the introduction of linkers to join variable domains of the invention to further protein sequences including immunoglobulin heavy chains, other variable domains (for example in the production of diabodies) or protein labels as discussed in more detail below.

Preferably, the specific binding molecule comprises a pair of binding domains based on the amino acid sequences for the VL and VH regions substantially as set out in FIG. 1. Single binding domains based on either of these sequences form further aspects of the invention. In the case of binding domains based on the amino acid sequence for the VH region substantially set out in FIG. 1, such binding domains may be used as targeting agents since it is known that immunoglobulin VH domains are capable of binding target antigens in a specific manner.

Specific binding molecules of the present invention may further comprise antibody constant regions or parts thereof. For example, specific binding molecules based on the VL region shown in FIG. 1 may be attached at their C-terminal end to antibody light chain constant domains including human CK or CA chains. Similarly, specific binding molecules based on VH region shown in FIG. 1 may be attached at their C-terminal end to all or part of an immunoglobulin heavy chain derived from any antibody isotype, e.g. IgG, IgA, IgE and IgM and any of the isotype sub-classes, particularly IgG1 and IgG4.

Specific binding molecules of the invention may additionally be labelled with a functional label Such functional labels include toxins such as ricin and enzymes such as bacterial carboxypeptidase or nitroreductase, which are capable of converting prodrugs into active drugs. In addition, the specific binding molecules may be attached or otherwise associated with chemotherapeutic or cytotoxic agents, such as calicheamicin, or radiolabels, such as $^{90}$Y or $^{131}$I.

Furthermore, specific binding molecules of the invention may be associated with additional therapeutic agent or targeting moiety. Therapeutic agents which may be associated with the specific binding molecules include immune-modulators and effectors, radioactive compounds, enzymes (perforin for example) or chemotherapeutic agents (cis-platin for example). To ensure that toxic effects are exercised in the desired location the toxin could be inside a liposome linked to the specific binding molecules so that the compound is released slowly. This will prevent damaging effects during the transport in the body and ensure that the toxin has maximum effect after binding of the specific binding molecules to the relevant antigen presenting cells.

Examples of suitable therapeutic agents include, but are not limited to:

small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate 10arbour10ate, aunstatin E vincristine and doxorubicin;

peptide cytotoxins, i.e. proteins or fragments thereof with the ability to kill mammalian cells. For example, ricin, diphtheria toxin, pseudomonas bacterial exotoxin A, Dnase and Rnase;

radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof.

Immuno-stimulants, i.e. immune effector molecules which stimulate immune response. For example, cytokines such as IL-2 and IFN-γ, Superantigens and mutants thereof;

TCR-HLA fusions, e.g. fusion to a peptide-HLA complex, wherein said peptide is derived from a common human pathogen, such as Epstein Barr Virus (EBV);

chemokines such as IL-8, platelet factor 4, melanoma growth stimulatory protein, etc;

antibodies or fragments thereof, including anti-T cell or NK cell determinant antibodies (e.g. anti-CD3, anti-CD28 or anti-CD16);

alternative protein scaffolds with antibody like binding characteristics complement activators.

xenogeneic protein domains, allogeneic protein domains, viral/bacterial protein domains, viral/bacterial peptides.

Targeting moieties which may be associated with the specific binding molecules include TCRs (including alpha/beta and gamma/delta TCRs)

antibodies or fragments thereof, that recognise and bind to antigens presented on target cells, including cell surface antigens and peptides derived from intracellular antigens that are presented on the cell surface in complex with MHC/HLA;

alternative protein scaffolds with antibody like binding characteristics

Furthermore, the specific binding molecules of the present invention may be administered alone or in combination with other treatments, either simultaneously or sequentially, dependent upon the condition to be treated. Thus, the present invention further provides products containing a specific binding molecule of the present invention and an active agent as a combined preparation for simultaneous, separate or sequential use in the treatment of a tumour. Active agents may include chemotherapeutic or cytotoxic agents including, 5-Fluorouracil, cisplatin, Mitomycin C, oxaliplatin and tamoxifen, which may operate synergistically with the binding molecules of the present invention. Other active agents may include suitable doses of pain relief drugs such as non-steroidal anti-inflammatory drugs (e.g. aspirin, paracetamol, ibuprofen or ketoprofen) or opiates such as morphine, or anti-emetics.

Specific binding molecules of the present invention will usually be administered in the form of a pharmaceutical composition, which may comprise at least one component in addition to the specific binding molecule. The pharmaceutical composition may comprise, in addition to active ingredient, a pharmaceutically acceptable excipient, diluent, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

It is envisaged that injections will be the primary route for therapeutic administration of the compositions although delivery through a catheter or other surgical tubing is also used Some suitable routes of administration include intravenous, subcutaneous and intramuscular administration. Liquid formulations may be utilised after reconstitution from powder formulations.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, anti-oxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the formulation is a liquid it may be, for example, a physiologic salt solution containing non-phosphate buffer at pH 6.8-7.6, or a lyophilised powder.

The composition may also be administered via microspheres, liposomes, other microparticulate delivery systems or sustained release formulations placed in certain tissues including blood. Suitable examples of sustained release carriers include semi-permeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1); 547-556, 1985), poly (2-hydroxyethyl-methacrylate) or ethylene vinyl acetate (Langer et al, J. Biomed. Mater. Res 15: 167-277, 1981, and Langer, Chem. Tech. 12.98-105, 1982). Liposomes containing the polypeptides are prepared by well-known methods: DE 3,218, 121A; Epstein et al, PNAS USA, 82: 3688-3692, 1985, Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

The composition may be administered in a localised manner to a desired site or may be delivered in a manner in which it targets the relevant cells.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0 nM is normally sufficient. For example, a dose of 100 mg/m2 of antibody provides a serum concentration of approximately 20 nM for approximately eight days.

As a rough guideline, doses of antibodies may be given weekly in amounts of 10-300 mg/m$^2$. Equivalent doses of antibody fragments should be used at more frequent intervals in order to maintain a serum level in excess of the concentration that permits saturation of the sialyltetraosyl carbohydrateceramide.

The dose of the composition will be dependent upon the properties of the binding molecule, e.g. its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 300 μg of antibody per patient per administration are preferred, although dosages may range from about 10 μg to 6 mg per dose. Different dosages are utilised during a series of sequential inoculations; the practitioner may administer an initial inoculation and then boost with relatively smaller doses of antibody.

The binding molecules of the present invention may be generated wholly or partly by chemical synthesis. The binding molecules can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Illinois (1984), in M. Bodanzsky and A. Bodanzsky, The Practice of Peptide Synthesis, Springer Verlag, New York (1984); and Applied Biosystems 430A Users Manual, ABI Inc., Foster City, California), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a binding molecule according to the present invention is to express the nucleic acid encoding it, by use of nucleic acid in an expression system.

The present invention further provides an isolated nucleic acid encoding a specific binding molecule of the present invention. Nucleic acid includes DNA and RNA. In a preferred aspect, the present invention provides a nucleic acid which codes for a specific binding molecule of the invention as defined above. The skilled person will be able to determine substitutions, deletions and/or additions to such nucleic acids which will still provide a specific binding molecule of the present invention.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding a specific binding molecule of the invention forms an aspect of the present invention, as does a method of production of the specific binding molecule which method comprises expression from encoding nucleic acid therefor. Expression may conveniently be achieved by culturing under appropriate conditions recombinant host cells containing the nucleic acid. Following production by expression, a specific binding molecule may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art. For a review, see for example Plückthun, Bio/Technology 9:545-551 (1991). Expression in eukaryotic cells in culture is also available to those skilled in the art as an option for production of a specific binding molecule, see for recent review, for example Reff, Curr. Opinion Biotech. 4:573-576 (1993); Trill et al., Curr. Opinion Biotech. 6:553-560 (1995).

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Sambrook et al, Molecular Cloning: A Laboratory Manual: 2nd Edition, Cold Spring Harbor Laboratory Press (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., Short Protocols in Molecular Biology, 2nd Edition, John Wiley & Sons (1992).

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene.

The nucleic acid of the invention may be integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding molecule or polypeptide as above.

In a further aspect, there is provided a bifunctional binding molecule comprising:
   i) T cell receptor (TCR) or antibody; and
   ii) a specific binding molecule which binds to CD3 according to the first aspect.

It will be understood that any and all features described above in respect of the first aspect are equally applicable to this further aspect.

The targeting moiety may be a T cell receptor (TCR), an antibody or an antibody fragment.

The arrangement of anti-CD3 and targeting moiety can be in any known format (such as described in Brinkman et al., *MAbs.* 2017 February-March; 9(2): 182-212, FIG. 2).

The T cell receptor (TCR) may be a heterodimeric alpha/beta or gamma/delta TCR polypeptide pair. The T cell receptor (TCR) may be a single chain TCR polypeptide.

The specific binding molecule which binds to CD3 may be fused to the C or N terminus of the alpha or beta chain of the T cell receptor (TCR). Preferably, the CD3 effector is fused to the N terminus of the beta chain of the TCR. The bifunctional binding molecule may be in the form of a diabody, in which the TCR-Va is attached to antiCD3-VL and the TCR-Vb is attached to the antiCD3-VH and vice versa.

In some cases the specific binding molecule which binds to CD3 may be is fused to the C or N terminus of the targeting moiety. In other cases, the specific binding molecule which binds to CD3 is fused to the C or N terminus of the targeting moiety via a linker The specific binding molecule which binds to CD3 may be fused to the T cell receptor (TCR) or a TCR-like antibody via a linker, which may be a polypeptide linker. Polypeptide linker sequences are usually flexible, in that they are made up of amino acids such as glycine, alanine and serine which do not have bulky side chains likely to restrict flexibility. Usable or optimum lengths of linker sequences are easily determined. Often the linker sequence will be less than about 12, such as less than 10, or from 5-10 amino acids in length The linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. A preferred linker includes a sequence with the formula (GGGGS)$_n$ (SEQ ID NO: 23), optionally in addition to other amino acids.

The TCR may comprise a non-native di-sulphide bond between the constant region of the alpha chain and the constant region of the beta chain.

The TCR may bind to MHC in complex with a peptide antigen. Preferably, the peptide antigen is any disease associated antigen. Preferably, the peptide antigen is any tumour associated antigen.

Preferably, the peptide antigen is a peptide derived from GP100, NYESO, MAGEA4, or PRAME as described in WO2011001152, WO2017109496, WO2017175006 and WO2018234319.

A suitable TCR may have an amino acid sequence as defined in WO2011001152, WO2017109496, WO2017175006 and WO2018234319.

The TCR may have an amino acid sequence as follows:

```
                                           (SEQ ID NO: 31)
DGGITQSPKYLFRKEGQNVTLSCEQNLNHDAMYWYRQDPGQGLRLIYYSQ

IMGDEQKGDIAEGYSVSREKKESFPLTVTSAQKNPTAFYLCASSVWVTGG

SAPIRFGPGTRLTVTEDLKNVFPPEVAVFEPSEAEISHTQKATLVCLATG

FYPDHVELSWWVNGKEVHSGVCTDPQPLKEQPALNDSRYALSSRLRVSAT

FWQDPRNHFRCQVQFYGLSENDEWTQDRAKPVTQIVSAEAWGRAD
``` or an amino acid sequence at least 70% identical thereto.

The bifunctional binding molecule may have an amino acid sequence as follows:

```
                                           (SEQ ID NO: 32)
AIQMTQSPSSLSASVGDRVTITCRASQDIRNYLNWYQQKPGKAPKLLIYY

TSRLESGVPSRFSGSGSGTDYTLTISSLQPEDFATYYCQQGNTLPWTFGQ

GTKVEIKGGGGSGGGGSGGGGSGGGGSGGGGSEVQLVESGGGLVQPGGSLR

LSCAASGYSFTGYAMNWVRQAPGKGLEWVALINPYKGVSTYNQKFKDRFT

ISVDKSKNTAYLQMNSLRAEDTAVYYCARSGYYGDSDWYFDVWGQGTLVT

VSSGGGGSDGGITQSPKYLFRKEGQNVTLSCEQNLNHDAMYWYRQDPGQG

LRLIYYSQIMGDEQKGDIAEGYSVSREKKESFPLTVTSAQKNPTAFYLCA

SSWWTGGSAPIRFGPGTRLTVTEDLKNVFPPEVAVFEPSEAEISHTQKAT

LVCLATGFYPDHVELSWWVNGKEVHSGVCTDPQPLKEQPALNDSRYALSS

RLRVSATFWQDPRNHFRCQVQFYGLSENDEWTQDRAKPVTQIVSAEAWGR

AD
``` or an amino acid sequence at least/0% identical thereto.

Or, the bifunctional binding molecule may have an amino acid sequence as follows:

```
                                           (SEQ ID NO: 33)
AIQMTQSPSSLSASVGDRVTITCRASQDIRNYLNWYQQKPGKAPKLLIYY

TSRLESGVPSRFSGSGSGTDYTLTISSLQPEDFATYYCQQGNTLPWTFGQ

GTKVEIKGGGGSGGGGSGGGGSGGGGSGGGGSEVQLVESGGGLVQPGGSLR

LSCAASGYSFTGYAMNWVRQAPGKGLEWVALINPYKGVSTYNQKFKDRFT

FSVDKSKNTAYLQMNSLRAEDTAVYYCARSGYYGDSDWYFDVWGQGTLVT

VSSGGGGSDGGITQSPKYLFRKEGQNVTLSCEQNLNHDAMYWYRQDPGQG
```

15

-continued

```
LRLIYYSQIMGDEQKGDIAEGYSVSREKKESFPLTVTSAQKNPTAFYLCA

SSWWTGGSAPIRFGPGTRLTVTEDLKNVFPPEVAVFEPSEAEISHTQKAT

LVCLATGFYPDHVELSWWVNGKEVHSGVCTDPQPLKEQPALNDSRYALSS

RLRVSATFWQDPRNHFRCQVQFYGLSENDEWTQDRAKPVTQIVSAEAWGR

AD
``` or an amino acid sequence at least 70% identical thereto.

Phenotypically silent variants of specific binding molecules or bifunctional binding molecules are also disclosed herein. As used herein the term "phenotypically silent variants" is understood to refer to a specific binding molecule or bifunctional binding molecule variable domain which incorporates one or more further amino acid changes, including substitutions, insertions and deletions, which molecule or molecule has a similar phenotype to the corresponding molecule or polypeptide without said change(s).

Phenotypically silent variants may contain one or more conservative substitutions and/or one or more tolerated substitutions. By tolerated substitutions it is meant those substitutions which do not fall under the definition of conservative as provided below but are nonetheless phenotypically silent. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains), lysine, arginine and histidine (amino acids having basic side chains); aspartate and glutamate (amino acids having acidic side chains); asparagine and glutamine (amino acids having amide side chains), and cysteine and methionine (amino acids having sulphur containing side chains). It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

Substitutions of this nature are often referred to as "conservative" or "semi-conservative" amino acid substitutions. The present invention therefore extends to use of a specific binding molecule or bifunctional binding molecule comprising any of the amino acid sequences described above but with one or more conservative substitutions and or one or more tolerated substitutions in the sequence, such that the amino acid sequence of the specific binding molecule or bifunctional binding molecule has at least 80% identity, or at least 90% identity, such as at least 90%, at least 91%, at least 92%, at least 93%, at least 94%, at least 95%, at least 96%, at least 97%, at least 98%, at least 99% or 100% identity, to the specific binding molecule or bifunctional binding molecule described above.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87.2264-2268, modified as in Karlin and Altschul (1993) Proc. Natl. Acad. Sci. USA 90:5873-5877. The BLASTn and BLASTp programs of Altschul, et al. (1990) J. Mol. Biol. 215:403-410 have incorporated such an algorithm. Determination of percent identity between two nucleotide sequences can be performed with the BLASTn program. Determination of percent identity between two protein sequences can be performed with the BLASTp program. To obtain gapped alignments for comparison purposes, Gapped BLAST can be utilised as described in Altschul et al. (1997) Nucleic Acids Res 25:3389-3402 Alternatively, PSI-Blast can be used to perform an iterated search which detects distant relationships between molecules (Id.). When utilising BLAST, Gapped BLAST, and PSI-Blast programs, the default parameters of the respective programs (e.g., BLASTp and BLASTp) can be used. See http://www.ncbi.nlm.nih.gov. Default general parameters may include for example, Word Size=3, Expect Threshold=10. Parameters may be selected to automatically adjust for short input sequences. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl Biosci., 10:3-5; and FASTA described in Pearson and Lipman (1988) Proc. Natl Acad Sci. 85:2444-8. Within FASTA, ktup is a control option that sets the sensitivity and speed of the search. For the purposes of evaluating percent identity in the present disclosure, BLASTp with the default parameters is used as the comparison methodology. In addition, when the recited percent identity provides a non-whole number value for amino acids (i.e., a sequence of 25 amino acids having 90% sequence identity provides a value of "22.5", the obtained value is rounded down to the next whole number, thus "22"). Accordingly, in the example provided, a sequence having 22 matches out of 25 amino acids is within 90% sequence identity.

As will be obvious to those skilled in the art, it may be possible to truncate, or extend, the sequences provided at the C-terminus and/or N-terminus thereof, by 1, 2, 3, 4, 5 or more residues, without substantially affecting the functional characteristics of the specific binding molecule. The sequences provided at the C-terminus and/or N-terminus thereof may be truncated or extended by 1, 2, 3, 4 or 5 residues. All such variants are encompassed by the present invention.

Mutations, including conservative and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual (3$^{rd}$ Ed) CSHL Press. Further information on ligation independent cloning (LIC) procedures can be found in Rashtchian, (1995) *Curr Opin Biotechnol* 6(1): 30-6. The sequences provided by the invention may be obtained from solid state synthesis, or any other appropriate method known in the art.

The targeting moiety may be an antibody or fragment thereof. Preferably, the antibodies, including fragments, derivatives and variants thereof, bind to antigens presented on diseased or cancerous cells.

Specific binding molecules or bifunctional binding molecules of the present invention can be used in methods of diagnosis and treatment of cancers or infectious diseases in human or animal subjects. Examples of cancers include but are not limited to liquid tumours such as Leukaemias, lymphomas and myeloma and solid tumours including bladder, breast, cervix, colorectal, esophogeal endometrial gastric, glioblastoma, liver, melanoma, lung, ovarian, pancreatic, prostate, sarcoma, thyroid.

Examples of infectious diseases include but are not limited to HIV, HBV, TB, HCV, When used in diagnosis, specific binding molecules or bifunctional binding molecules of the invention may be labelled with a detectable label, for example a radiolabel such as $^{131}$I or $^{99}$Tc, which may be attached to specific binding molecules of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Specific binding molecules or bifunctional binding molecule of the invention may be amenable to high yield purification, particularly specific binding molecules in soluble format. Yield may be determined based on the amount of material retained during the purification process (i.e. the amount of correctly folded material obtained at the end of the purification process relative to the amount of solubilised material obtained prior to refolding), and or yield may be based on the amount of correctly folded material obtained at the end of the purification process, relative to the original culture volume. High yield means greater than 1%, or more preferably greater than 5%, or higher yield. High yield means greater than 1 mg/ml, or more preferably greater than 3 mg/ml, or greater than 5 mg/ml, or higher yield.

Methods to determine binding affinity (inversely proportional to the equilibrium constant $K_D$) and binding half life (expressed as T½) are known to those skilled in the art. Preferably, binding affinity and binding half-life are determined using Surface Plasmon Resonance (SPR) or Bio-Layer Interferometry (BLI), for example using a BIAcore instrument or Octet instrument, respectively. It will be appreciated that doubling the affinity results in halving the $K_D$. T½ is calculated as ln 2 divided by the off-rate ($k_{off}$). Therefore, doubling of T½ results in a halving in $k_{off}$. $K_D$ and $k_{off}$ values. To account for variation between independent measurements, and particularly for interactions with dissociation times in excess of 20 hours, the binding affinity and or binding half-life of a given molecule may be measured several times, for example 3 or more times, using the same assay protocol, and an average of the results taken. To compare binding data between two samples (i.e. two different molecules and/or two preparations of the same molecule) it is preferable that measurements are made using the same assay conditions (e.g. temperature), such as those described in WO2018234319.

TCRs described herein may be αβ heterodimers. Alpha-beta heterodimeric TCRs usually comprise an alpha chain TRAC constant domain sequence and/or a beta chain TRBC1 or TRBC2 constant domain sequence. The constant domains may be full-length by which it is meant that extracellular, transmembrane and cytoplasmic domains are present, or they may be in soluble format (i.e. having no transmembrane or cytoplasmic domains). One or both of the constant domains may contain mutations, substitutions or deletions relative to the native TRAC and/or TRBC1/2 sequences. The term TRAC and TRBC1/2 also encompasses natural polymorphic variants, for example N to K at position 4 of TRAC (Bragado et al International immunology. 1994 February; 6(2):223-30).

For soluble TCRs, the alpha and beta chain constant domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may have an introduced disulphide bond between residues of the respective constant domains, as described, for example, in WO 03/020763. The alpha and beta constant domains may be modified by substitution of cysteine residues at position Thr 48 of TRAC and position Ser 57 of TRBC1 or TRBC2, the said cysteines forming a disulphide bond between the alpha and beta constant domains of the TCR. TRBC1 or TRBC2 may additionally include a cysteine to alanine mutation at position 75 of the constant domain and an asparagine to aspartic acid mutation at position 89 of the constant domain. One or both of the extracellular constant domains present in an ap heterodimer may be truncated at the C terminus or C termini, for example by up to 15, or up to 10, or up to 8 or fewer amino acids. One or both of the extracellular constant domains present in an ap heterodimer may be truncated at the C terminus or C termini by, for example, up to 15, or up to 10 or up to 8 amino acids. The C terminus of the alpha chain extracellular constant domain may be truncated by 8 amino acids. Soluble TCRs are preferably associated with therapeutic agents and/or detectable labels.

The constant domains of an as heterodimeric TCR may be full length, having both transmembrane and cytoplasmic domains. Such TCRs may contain a disulphide bond corresponding to that found in nature between the respective alpha and beta constant domains. Additionally, or alternatively, a non-native disulphide bond may be present between the extracellular constant domains Said non-native disulphide bonds are further described in WO03020763 and WO06000830. The non-native disulphide bond may be between position Thr 48 of TRAC and position Ser 57 of TRBC1 or TRBC2. One or both of the constant domains may contain one or more mutations substitutions or deletions relative to the native TRAC and/or TRBC1/2 sequences TCRs with full-length constant domains are preferable for use in adoptive therapy.

TCRs described herein may be in single chain format. Single chain formats include, but are not limited to, as TCR polypeptides of the Vα-L-Vβ, VS-L-Vα, Vα-Cα-L-Vβ, Vα-L-Vβ-Cβ, or Vα-Cα-L-Vβ-Cβ types, wherein Vα and Vβ are TCR α and β variable regions respectively, Cα and Cβ are TCR α and β constant regions respectively, and L is a linker sequence (Weidanz et al., (1998) J Immunol Methods. December 1; 221(1-2):59-76; Epel et al., (2002), Cancer Immunol Immunother. November; 51(10):565-73; WO 2004/033685; WO9918129). Where present, one or both of the constant domains may be full length, or they may be truncated and/or contain mutations as described above. Preferably single chain TCRs are soluble. Single chain TCRs may have an introduced disulphide bond between residues of the respective constant domains, as described in WO 2004/033685. Single chain TCRs are further described in WO2004/033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

Specific binding molecules or bifunctional binding molecules may be associated (covalently or otherwise) with a PK modifying moiety. Examples of PK modifying moieties include, but are not limited to, PEG (Dozier et al., (2015) Int J Mol Sci. October 28; 16(10):25831-64 and Jevsevar et al., (2010) Biotechnol J. January; 5(1):113-28), PASylation (Schlapschy et al., (2013) Protein Eng Des Sel. August; 26(8):489-501), albumin, and albumin binding domains, (Dennis et al., (2002) J Biol Chem. September 20; 277(38): 35035-43), and/or unstructured polypeptides (Schellenberger et al., (2009) Nat Biotechnol. December; 27(12): 1186-90). Further PK modifying moieties include antibody Fc fragments.

As used herein, the term "antibody" encompasses such fragments and variants. Antibody fragments and variants/ analogues which are suitable for use in the compositions and methods described herein include minibodies, Fab fragments, F(ab')2 fragments, dsFv and scFv fragments, diabodies, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (*Pieris* (Germany)), comprising engineered anticalins) to name but a few.

Antibody also includes TCR-like antibodies (Chang et al., Expert Opin Biol Ther. 2016 August; 16(8):979-87 and Dahan et al., Expert Rev Mol Med. 2012 Feb. 24; 14:e6).

Linkage of the targeting moiety and specific binding molecule of the first aspect may be via covalent or non-covalent attachment Covalent attachment may be direct, or indirect via a linker sequence Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length, preferably 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers that may be used in TCRs of the invention include, but are not limited to: GGGSGGGG (SEQ ID NO: 22), GGGGS (SEQ ID NO: 23), GGGSG (SEQ ID NO: 24), GGSGG (SEQ ID NO: 25), GSGGG (SEQ ID NO: 26), GSGGGP (SEQ ID NO: 27), GGEPS (SEQ ID NO: 28), GGEGGGP (SEQ ID NO. 29), and GGEGGGSEGGGS (SEQ ID NO. 30) (as described in WO2010/133828).

As is well-known in the art, specific binding molecules or bifunctional binding molecules may be subject to post translational modifications. Glycosylation is one such modification, which comprises the covalent attachment of oligosaccharide moieties to defined amino acids in the amino acid chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody based therapeutics. (Jefferis et al., (2009) Nat Rev Drug Discov March; 8(3):226-34). For soluble TCRs glycosylation may be controlled, by using particular cell lines for example (including but not limited to mammalian cell lines such as Chinese hamster ovary (CHO) cells or human embryonic kidney (HEK) cells), or by chemical modification. Such modifications may be desirable, since glycosylation can improve pharmacokinetics, reduce immunogenicity and more closely mimic a native human protein (Sinclair and Elliott, (2005) Pharm Sci August; 94(8):1626-35).

For administration to patients, the specific binding molecules, bifunctional binding molecules, nucleic acids, expression vectors or cells of the invention may be provided as part of a sterile pharmaceutical composition together with one or more pharmaceutically acceptable carriers or excipients. This pharmaceutical composition may be in any suitable form. (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, intrathecal or intravenous), enteral (including oral or rectal), inhalation or intranasal routes Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. a suitable dose range for molecule of the invention may be in the range of 25 ng/kg to 50 µg/kg or 1 µg to 1 g. A physician will ultimately determine appropriate dosages to be used Specific binding molecules, bifunctional binding molecules, pharmaceutical compositions, vectors, nucleic acids and cells of the invention may be provided in substantially pure form, for example, at least 80%, at least 85%, at least 90%, at least 91%, at least 92%, at least 93%, at least 94%, at least 95%, at least 96%, at least 97%, at least 98%, at least 99% or 100% pure.

The method of treatment may further include administering separately, in combination, or sequentially, an additional anti-neoplastic agent. Example of such agents are known in the art and may include immune activating agents and/or T cell modulating agents.

Nucleic acids, expression vectors, host cells and methods of production as described above in relation to the first aspect are also contemplated in relation to the other aspects described herein.

Preferred features of each aspect of the invention are as for each of the other aspects mutatis mutandis. The prior art documents mentioned herein are incorporated by reference to the fullest extent permitted by law.

DESCRIPTION OF THE DRAWINGS

FIG. 1—provides VH and VL amino acid sequences of improved UCHT1 variants. CDRs are underlined. Mutations are shown in bold. FIG. 1 contains SEQ ID NOS 16 and 18-19, respectively, in order of appearance.

FIG. 2—provides example amino acid sequences a TCR-anti-CD3 fusion protein, incorporating improved anti-CD3 scFv variants. FIG. 2 contains SEQ ID NOS 34 and 32-33, respectively, in order of appearance.

FIG. 3—demonstrates a TCR-CD3 fusion incorporating improved anti-CD3 scFv variant 1 has a better therapeutic window relative to non-mutated anti-CD3 (A) and a TCR-CD3 fusion incorporating improved anti-CD3 scFv variant 2 has a higher Emax relative to non-mutated anti-CD3 (B) FIG. 4—demonstrates improved T cell killing properties mediated by a TCR-CD3 fusion incorporating UCHT1 variant 1 and variant 2.

Figure 4:
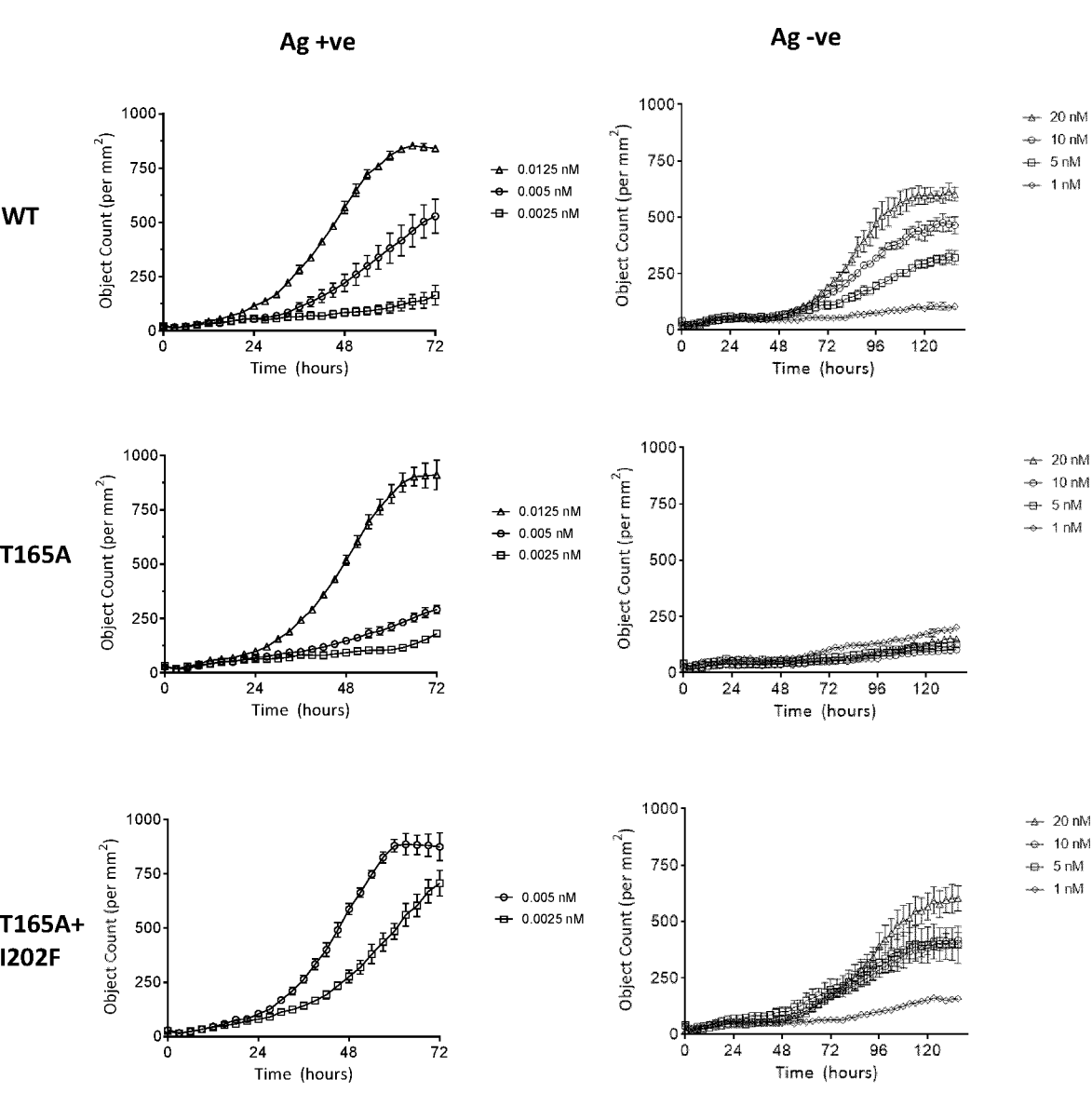

The invention is further described in the following non-limiting examples.

EXAMPLES

The following examples describe bifunctional binding molecules of the invention, which may be referred to as TCR-antiCD3-bispecific proteins.
1) Preparation of TCR-Anti-CD3 Bispecific Fusion Proteins with Improved Anti-CD3

Fusion proteins comprising a TCR and an anti-CD3 scFv are known in the art (for example, see WO2011001152, WO2017109496, WO2017175006 and WO2018234319). These molecules comprise a humanised UCHT1 scFv fragment.

In this example, variants of a TCR-anti-CD3 fusion protein described in WO2018234319 were produced that incorporate either anti-CD3 variant 1 (T165A) or anti-CD3 variant 2 (T165A+I202F). Mutations were introduced using standard mutagenesis and cloning methods (such as described in Sambrook, Joseph. (2001). Molecular cloning: a laboratory manual. Cold Spring Harbor, N.Y.: Cold Spring Harbor Laboratory Press). Amino acid sequences of VL and VH for T165A and T165A+I202F are provided in FIG. 1. Amino acids sequences of a TCR-anti-CD3 incorporating the sequences provided in FIG. 1 are provided in FIG. 2.

TCR-anti-CD3 fusion proteins comprising T165A, T165A+I202F or non-mutated (WT) UCHT1 scFv were expressed in E. coli as inclusion bodies and subsequently refolded and purified using the methods described in WO2018234319, example 2)

2) Increased Therapeutic Window and Maximum T Cell Activation Mediated by TCR-and-CD3 with Variants T165A and T165A+I202F A) IFN-γ Release The TCR-anti-CD3 fusion proteins described above were assessed for their ability to mediate activation of CD3+ T cells in the presence of antigen positive and antigen negative cells. Interferon-γ (IFN-γ) release was used as a read out for T cell activation.

Assays were performed using a human IFN-γ ELISPOT kit (BD Biosciences) according to the manufacturer's instructions. Briefly, Me1624 melanoma cells were used as antigen positive target cells. Granta-519 B cell lymphoma cells were used as antigen negative target cells. Target cells were prepared at a density of $1 \times 10^6$/ml in assay medium (RPMI 1640 containing 10% heat inactivated FBS and 1% penicillin-streptomycin-L-glutamine) and plated at 50,000 cells per well in a volume of 50 µl. Peripheral blood mononuclear cells (PBMC), isolated from fresh donor blood, were used as CD3+ effector cells and plated at 35,000 cells per well in a volume of 50 µl. TCR-anti-CD3 proteins were titrated to final concentrations of between 10 nM and 0.0001 nM, and added to the well in a volume of 50 µl.

Plates were prepared and developed according to the manufacturer's instructions. Wells containing target cells, effector cells and fusion proteins were made up to a final volume of 200 µl with assay medium. All reactions were performed in triplicate. Control wells were also prepared with the omission of, either fusion protein, effector cells, or target cells. The plates were incubated overnight (37° C./5% $CO_2$). The next day the plates were washed three times with wash buffer (1×PBS sachet, containing 0.05% Tween-20, made up in deionised water). Primary detection antibody was then added to each well in a volume of 50 µl. Plates were incubated at room temperature for 2 hours prior to being washed again three times. Secondary detection was performed by adding 50 µl of diluted streptavidin-HRP to each well and incubating at room temperature for 1 hour and the washing step repeated. No more than 15 mins prior to use, one drop (20 µl) of AEC chromogen was added to each 1 ml of AEC substrate and mixed and 50 µl added to each well Spot development was monitored regularly and plates were washed in tap water to terminate the development reaction. The plates were then allowed to dry at room temperature for at least 2 hours prior to counting the spots using a CTL analyser with Immunospot software (Cellular Technology Limited). Data were prepared and analysed using PRISM software.

The therapeutic window was calculated by determining the relative potency of T cell activation mediated by TCR-antiCD3 variant and WT, against antigen-positive cells, and comparing Ec50 values after curve-fitting in Prism. For antigen-negative cells robust Ec50 values could not be obtained, so a 'minimal cross-reactive concentration' was determined by setting a threshold number of spots (eg. 25 spots per well), and identifying by interpolation the concentration that would first exceed that number.

Results

T165A

To obtain a robust determination of therapeutic window, data were averaged from 4 Ag+ plates and 4 Ag-plates each of which had non-mutated and T165A side-by-side. FIG. 3A shows the curves obtained from one plate. Data for each of the individual plates is shown in the tables below.

|  | Plate 1 | Plate 2 | Plate 5 | Plate 6 |
|---|---|---|---|---|
| Target cells | Mel 624 (Ag+) | Mel 624 (Ag+) | Mel 624 (Ag+) | Mel 624 (Ag+) |
| Effector cells | Donor 1 | Donor 1 | Donor 2 | Donor 2 |
| T165A EC50 | 116 pM | 137 pM | 160 pM | 446 pM |
| Wt EC50 | 62.2 pM | 60.9 pM | 79.3 pM | 72.1 pM |
| T165A relative potency | 0.54 | 0.44 | 0.50 | 0.16 |

|  | Plate 3 | Plate 4 | Plate 7 | Plate 8 |
|---|---|---|---|---|
| Target cells | Granta 519 (Ag-) | Granta 519 (Ag-) | Granta 519 (Ag-) | Granta 519 (Ag-) |
| Effector cells | Donor 1 | Donor 1 | Donor 2 | Donor 2 |
| T165A cross-reactive concentration | 1.56 nM | 7.16 nM | 0.698 nM | 0.615 nM |
| Wt cross-reactive concentration | 0.165 nM | 0.811 nM | 0.206 nM | 0.152 nM |
| T165A relative cross-reactivity | 0.11 | 0.11 | 0.29 | 0.25 |

The relative potency against antigen positive cells (i.e. Ec50 of WT divided by Ec50 of T165A) gave an average of 0.41. The relative cross-reactivity against antigen negative cells (i.e. conc of WT giving 25 spots/concentration of T165A giving 25 spots) gave an average of 0.19. These data demonstrate that the therapeutic window of T165A is approximately 2x greater than the window for the WT.

T165A+I202F

FIG. 3B shows that the T165A+I202F variant results in a higher maximum T cell activation (Emax) relative to WT. In this case the therapeutic window is similar to WT. These data demonstrate that T165A+I202F is more efficient at activating T cells.

B) T Cell Mediated Killing

The ability of TCR-anti-CD3 fusion proteins to mediate redirected T cell killing of antigen positive and antigen negative tumour cells was investigated using the IncuCyte platform (Essen BioScience). This assay allows real time detection by microscopy of the release of Caspase-317, a marker for apoptosis.

Method

Assays were performed using the CellPlayer 96-well Caspase-3/7 apoptosis assay kit (Essen BioScience, Cat. No.

4440) and carried out according the manufacturers protocol. Briefly, target cells (Me1624 (antigen positive) or MDA MB 231 (antigen negative) cells were plated at 10,000 cells per well and incubated overnight to allow them to adhere. TCR-anti-CD3 fusion proteins were added at concentrations between 0.05 nM and 0.0125 nM (for antigen positive cells) and between 20 nM and 0.125 nM (for antigen negative cells). CD3+ effector cells (PBMC) were used at an effector target cell ratio of 10:1 (100,000 cells per well). NucView assay reagent was made up at 30 µM and 25 µl added to every well and the final volume brought to 150 µl (giving 5 µM final conc). The plate was placed in the IncuCyte instrument and images at regular intervals over 3 to 5 days. The number of apoptotic cells in each image was determined and recorded as object count per $mm^2$. Assays were performed in triplicate. Graphs were prepared using PRISM software.

Results

The resulting killing curves for WT, T165A and T165A+I202F against antigen positive and antigen negative cells are shown in FIG. 4. Note that for clarity, only the curves for the indicated concentrations are shown.

T165A

T165A shows a small reduction in T cell killing of antigen positive cells relative to WT at a concentration of 0.005 nM. Killing of antigen negative cells is not observed up to 20 nM whereas for WT killing is observed at a concentration of 1 nM. These data confirm the above findings that T165A has an improved therapeutic window.

T165A+I202F

T165A+I202F shows increase in T cell mediated killing at a given concentration (e.g. 0.005 nM) against antigen positive cells. Killing of antigen negative cells is comparable to WT. These data confirm the above findings and demonstrate that T165A+I202F is more efficient at activating T cells.

The data presented in the example demonstrate that TCR-antiCD3 fusion proteins incorporating T165A or T165A+I202F UCHT1 variants have improved therapeutic properties

The invention claimed is:

1. An antibody or antibody fragment thereof that specifically binds to CD3, comprising an immunoglobulin variable light chain (VL) domain and an immunoglobulin variable heavy chain (VH) domain, wherein the immunoglobin VL domain comprises the sequence:

```
                                      (SEQ ID NO: 16)
AIQMTQSPSSLSASVGDRVTITCRASQDIRNYLNWYQQKPGKAPKLLIY

YTSRLESGVPSRFSGSGSGTDYTLTISSLQPEDFATYYCQQGNTLPWTF

GQGTKVEIK;
``` and
the immunoglobulin VH domain comprises the sequence:

```
                                      (SEQ ID NO: 18)
EVQLVESGGGLVQPGGSLRLSCAASGYSFTGYAMNWVRQAPGKGLEWVAL

INPYKGVSTYNQKFKDRFTISVDKSKNTAYLQMNSLRAEDTAVYYCARSG

YYGDSDWYFDVWGQGTLVTVSS;
or
                                      (SEQ ID NO: 19)
EVQLVESGGGLVQPGGSLRLSCAASGYSFTGYAMNWVRQAPGKGLEWVAL

INPYKGVSTYNQKFKDRFTFSVDKSKNTAYLQMNSLRAEDTAVYYCARSG

YYGDSDWYFDVWGQGTLVTVSS.
```

2. The antibody or antibody fragment thereof of claim 1, comprising a single chain variable fragment (scFv) molecule.

3. The antibody or antibody fragment thereof of claim 1, wherein the immunoglobin VL domain and the immunoglobulin VH domain are connected via a linker.

4. A fusion polypeptide comprising:
i) a targeting moiety selected from a T cell receptor (TCR), an antibody, or an antibody fragment; and
ii) the antibody or antibody fragment thereof of claim 1.

5. The fusion polypeptide of claim 4, wherein the TCR is a heterodimeric alpha/beta TCR polypeptide pair or a single chain alpha/beta TCR polypeptide.

6. The fusion polypeptide of claim 4, wherein the TCR comprises a non-native disulfide bond between the constant region of the alpha chain and the constant region of the beta chain.

7. The fusion polypeptide of claim 4, wherein the antibody or antibody fragment thereof is fused to the C terminus or the N terminus of the targeting moiety, optionally via a linker.

8. A pharmaceutical composition comprising the antibody or antibody fragment thereof of claim 1.

9. A nucleic acid molecule encoding the antibody or antibody fragment thereof of claim 1.

10. An expression vector comprising the nucleic acid molecule of claim 9.

11. An isolated host cell comprising the expression vector of claim 10, wherein the nucleic acid encoding the antibody or antibody fragment thereof is present as a single open reading frame or two distinct open reading frames.

12. A method of making an antibody or antigen binding fragment thereof that specifically binds to CD3, comprising culturing the isolated host cell of claim 11 under conditions for expression of a nucleic acid encoding the antibody or antibody fragment thereof and isolating the antibody or antibody fragment thereof.

13. The antibody or antibody fragment thereof of claim 1, wherein the immunoglobin VL domain comprises the sequence:

```
                                      (SEQ ID NO: 16)
AIQMTQSPSSLSASVGDRVTITCRASQDIRNYLNWYQQKPGKAPKLLIY

YTSRLESGVPSRFSGSGSGTDYTLTISSLQPEDFATYYCQQGNTLPWTF

GQGTKVEIK;
``` and
the immunoglobin VH domain comprises the sequence:
EVQLVESGGGLVQPGGSLRLSCAASGYSFTG-
YAMNWVRQAPGKGLEWVALINPYK
GVSTYNQKFKDRFTFSVDKSKNTAYLQMNSL-
RAEDTAVYYCARSGYYGDS DWYFDVWG-
QGTLVTVSS (SEQ ID NO: 19).

14. The antibody or antibody fragment thereof of claim 2, wherein the scFv molecule has the sequence:

```
                                      (SEQ ID NO: 21)
AIQMTQSPSSLSASVGDRVTITCRASQDIRNYLNWYQQKPGKAPKLLIY

YTSRLESGVPSRFSGSGSGTDYTLTISSLQPEDFATYYCQQGNTLPWTF

GQGTKVEIKGGGGSGGGGSGGGGSGGGGSGGGSEVQLVESGGGLVQPGG

SLRLSCAASGYSFTGYAMNWVRQAPGKGLEWVALINPYKGVSTYNQKFK

DRFTFSVDKSKNTAYLQMNSLRAEDTAVYYCARSGYYGDSDWYFDVWGQ

GTLVTVSS.
```

15. The antibody or antibody fragment thereof of claim 1, wherein the immunoglobin VL domain comprises the sequence:

```
                                   (SEQ ID NO: 16)
AIQMTQSPSSLSASVGDRVTITCRASQDIRNYLNWYQQKPGKAPKLLIY

YTSRLESGVPSRFSGSGSGTDYTLTISSLQPEDFATYYCQQGNTLPWTF

GQGTKVEIK;
``` and the immunoglobin VH domain comprises the sequence:

```
                                   (SEQ ID NO: 18)
EVQLVESGGGLVQPGGSLRLSCAASGYSFTGYAMNWVRQAPGKGLEWVA

LINPYKGVSTYNQKFKDRFTISVDKSKNTAYLQMNSLRAEDTAVYYCAR

SGYYGDSDWYFDVWGQGTLVTVSS.
```

16. The antibody or antibody fragment thereof of claim 2, wherein the scFv molecule has the sequence:

```
                                   (SEQ ID NO: 20)
AIQMTQSPSSLSASVGDRVTITCRASQDIRNYLNWYQQKPGKAPKLLIY

YTSRLESGVPSRFSGSGSGTDYTLTISSLQPEDFATYYCQQGNTLPWTF

GQGTKVEIKGGGGSGGGGSGGGGSGGGGSGGGSEVQLVESGGGLVQPGG

SLRLSCAASGYSFTGYAMNWVRQAPGKGLEWVALINPYKGVSTYNQKFK

DRFTISVDKSKNTAYLQMNSLRAEDTAVYYCARSGYYGDSDWYFDVWGQ

GTLVTVSS.
```

17. An antibody or antigen binding fragment thereof that specifically binds to CD3 comprising an immunoglobulin VL domain comprising Complementarity Determining Regions (CDRs) VLCDR1, VLCDR2, and VLCDR3, and an immunoglobulin VH domain comprising CDRs VHCDR1, VHCDR2, and VHCDR3, wherein the amino acid sequence of;

```
VLCDR1 is
                                   (SEQ ID NO: 1)
QDIRNY;

VLCDR2 is
YTS;
```

-continued

```
VLCDR3 is
                                   (SEQ ID NO: 2)
QQGNTLPWT;

VHCDR1 is
                                   (SEQ ID NO: 3)
GYSFTGYA;

VHCDR2 is
                                   (SEQ ID NO: 4)
INPYKGVS; and

VHCDR3 is
                                   (SEQ ID NO: 5)
ARSGYYGDSDWYFDV.
```

18. A heterodimeric TCR-anti-CD3 antibody fusion molecule, comprising:
   (a) a first polypeptide chain that comprises a TCR alpha chain variable domain; and
   (b) a second polypeptide chain that comprises a TCR beta chain variable domain fused to an anti-CD3 scFv having the amino acid sequence:

```
                                   (SEQ ID NO: 20)
AIQMTQSPSSLSASVGDRVTITCRASQDIRNYLNWYQQKPGKAPKLLIY

YTSRLESGVPSRFSGSGSGTDYTLTISSLQPEDFATYYCQQGNTLPWTF

GQGTKVEIKGGGGSGGGGSGGGGSGGGGSGGGSEVQLVESGGGLVQPGG

SLRLSCAASGYSFTGYAMNWVRQAPGKGLEWVALINPYKGVSTYNQKFK

DRFTISVDKSKNTAYLQMNSLRAEDTAVYYCARSGYYGDSDWYFDVWGQ

GTLVTVSS; or (SEQ ID NO: 21)
AIQMTQSPSSLSASVGDRVTITCRASQDIRNYLNWYQQKPGKAPKLLIY

YTSRLESGVPSRFSGSGSGTDYTLTISSLQPEDFATYYCQQGNTLPWTF

GQGTKVEIKGGGGSGGGGSGGGGSGGGGSGGGSEVQLVESGGGLVQPGG

SLRLSCAASGYSFTGYAMNWVRQAPGKGLEWVALINPYKGVSTYNQKFK

DRFTFSVDKSKNTAYLQMNSLRAEDTAVYYCARSGYYGDSDWYFDVWGQ

GTLVTVSS.
```

19. The antibody or antibody fragment thereof of claim 3, wherein the linker comprises between 5 amino acid residues to 30 amino acid residues.

\* \* \* \* \*